(12) United States Patent
Gosselink et al.

(10) Patent No.: US 6,649,689 B2
(45) Date of Patent: *Nov. 18, 2003

(54) HYDROPHILIC CURABLE ETHOXYLATED SILICONES

(75) Inventors: Eugene Paul Gosselink, Cincinnati, OH (US); Toan Trinh, Maineville, OH (US); Robb Richard Gardner, Cleves, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/996,870

(22) Filed: Nov. 15, 2001

(65) Prior Publication Data

US 2002/0120057 A1 Aug. 29, 2002

Related U.S. Application Data

(60) Provisional application No. 60/249,234, filed on Nov. 16, 2000.

(51) Int. Cl.⁷ .............................................. C08L 83/10
(52) U.S. Cl. ..................... 524/588; 528/38; 528/37; 106/287.11; 106/287.16; 427/387; 556/444; 556/445; 556/413; 556/424; 428/447; 442/93; 442/102; 442/106; 442/112; 442/119; 525/477
(58) Field of Search ................ 528/38, 37; 106/287.11, 106/287.16; 427/387; 556/444, 445, 413, 424; 428/447; 442/93, 102, 106, 112, 119; 524/588; 525/477; 523/105

(56) References Cited

U.S. PATENT DOCUMENTS

| 4,246,423 | A |   | 1/1981 | Martin |
| 4,800,026 | A |   | 1/1989 | Coffindaffer et al. |
| 5,677,269 | A |   | 10/1997 | Fost et al. |
| 5,683,685 | A | * | 11/1997 | Hirano et al. |
| 5,969,077 | A |   | 10/1999 | Schröck et al. |

FOREIGN PATENT DOCUMENTS

EP 0 803 527 A1 10/1997

* cited by examiner

*Primary Examiner*—Robert Dawson
*Assistant Examiner*—Kuo-Liang Peng
(74) *Attorney, Agent, or Firm*—Mark A. Charles; Jason J. Camp; Kim William Zerby

(57) ABSTRACT

This invention relates to hydrophilic curable alkoxylated silicone polymers for surface modification and are useful in, e.g., fiber and fabric care, hair care, skin care, surface care, and car care compositions. The compounds are curable silicone polymers which contain one or more polyalkyleneoxy groups, preferably polyalkyleneoxy pendant groups, comprising at least some ethyleneoxy units, said polyalkyleneoxy pendant groups are preferably capped with low molecular weight alkyl groups, such as $C_1$–$C_6$ alkyl groups. These compounds are substantive to the surface but keep the surface hydrophilic.

45 Claims, No Drawings

HYDROPHILIC CURABLE ETHOXYLATED SILICONES

CROSS REFERENCE TO RELATED APPLICATION

This application claims the benefit of provisional application No. 60/249,234 filed Nov. 16, 2000.

TECHNICAL FIELD

This invention relates to hydrophilic, curable, alkoxylated silicone polymers for surface modification and are useful in, e.g., fiber and fabric care, hair care, skin care, pet care, hard surface care, soft surface care, and car care compositions. The compounds are curable silicone polymers which contain one or more polyalkyleneoxy groups, preferably pendant groups, comprising at least some ethyleneoxy units, said polyalkyleneoxy pendant groups are preferably capped with low molecular weight non-reactive capping groups, such as $C_1$–$C_6$ alkyl groups. These compounds are substantive to the surface but keep the surface hydrophilic.

BACKGROUND OF THE INVENTION

Curable silicones comprise silicones having reactive functional groups that can further condense to form higher molecular weight polymers. One type of curable silicones of particular interest is the so-called room temperature vulcanizable (RTV) silicones that typically undergo condensation involving silanol functions. The silanol functions can be produced from other reactive functional groups, usually through reaction with water. Typical reactive functional groups include Si—H, Si—OH, and Si—OR groups, wherein R is typically a low molecular weight alkyl group or an acyl group. Two reactive functional groups of two separate silicone polymeric molecules, usually in the presence of moisture, can condense to form an Si—O—Si bond, thus in effect extending the silicone molecular backbone and forming a new silicone with higher molecular weight. The reactive functional groups can also form covalent bonds with the different surfaces to which the silicones are applied, when such surfaces have suitable functional groups that can react with the reactive functional groups of the silicones. Many curable silicones also contain amine functional groups to provide catalysis for the condensation reaction and/or additional surface substantivity benefit. These properties make curable silicones useful in surface protection and/or modification.

Curable amine functional silicones are broadly used in, e.g., car waxes and polishes to protect, e.g., painted, rubber and vinyl surfaces, such as those disclosed in U.S. Pat. No. 3,960,575 issued Jun. 1, 1976 to Martin, U.S. Pat. No. 3,576,779 issued Apr. 27. 1971 to Holdstock et al., said patents are incorporated herein by reference. Noncurable aminofunctional silicones are also disclosed for use in car care, such as U.S. Pat. No. 4,247,330 issued Jan. 27, 1981 to Sanders, said patent is incorporated herein by reference. Other applications are known. U.S. Pat. Nos. 4,800,026 issued Jan. 24, 1989 and 4,911,852 issued Mar. 27, 1990 to Coffindaffer et al. discloses the use of curable amino functional silicones for fabric wrinkle reduction; U.S. Pat. No. 4,419,391 issued Dec. 6, 1983 to Tanaka et al., discloses the use of curable amino silicones to impart fabrics with softness, slipperiness and sliminess; U.S. Pat. No. 5,098,979 issued Mar. 24, 1992 and U.S. Pat. No. 5,196,499 Issued Mar. 23, 1993 to O'Lenick, disclose noncurable polyethoxylated silicones with polyethoxylate groups capped by cationic groups comprising long chain alkyl groups for use as softener actives; said patents describe various examples of curable amino functional silicones, and are incorporated herein by reference. U.S. Pat. No. 5,091,105 issued Feb. 25, 1992 to Madore et al. discloses the use of hydrophobic curable silicones not containing amino substituents to provide fabric softening benefit in liquid detergent compositions; said patent is incorporated herein by reference.

Typical curable silicones, such as curable amine functional silicones, are surface substantive and make the treated surface very hydrophobic. The surface hydrophobicity is a desired property for some applications, such as car care. A car painted surface treated with curable silicone-containing wax is very water repellent, and causes water to bead up to form distinctive water drops on the car painted surface. This phenomenon is used as a signal for the protection benefit of the wax treatment.

However, the surface hydrophobicity, water repellent property is not desirable in other applications. When a car is treated with curable silicones and then exposed to rain or splashed water on the road, the water drops on the car surface frequently contain dirt and other soils that become visible when these distinctive water drops dry out. This results in nonuniformly soiled spots on the surface that are unsightly and undesirable. On the other hand, a hydrophilic car surface provides a sheeting action with which rain or splashed water can wet and spread across the car surface uniformly, forming a continuous film that is largely drained away and helps the soil run off, or at least spreads the soil more uniformly on the car surface. When the car surface dries out, the soil, if any, is distributed more uniformly, and becomes significantly less visible and more acceptable.

For normal usage, waterproofing of garments and other household fabrics such as towels is also not desirable and should be avoided.

Therefore, it is desirable for many applications, such as in and fabric care, hair care, skin care, pet care, and car care compositions, to have silicone polymers as surface modifiers that keep or make the treated surface hydrophilic. Thus the present invention relates to curable silicones that are surface substantive, but without the accompanying hydrophobicity negative. This surface substantivity results in long lasting benefits, such as fabric color restoration, fabric softening, fabric conditioning, wrinkle control, soil release, and antistatic properties, without the fabrics becoming hydrophobic. It also results in, e.g., long lasting car care benefits, e.g., shine/gloss, color deepening, glide/lubricity, and long lasting hair care benefits, such as shine and easy combing.

SUMMARY OF THE INVENTION

The present invention relates to a class of novel curable silicone polymers comprising:
(a) one or more reactive Si functional groups including Si—H, Si—OH, Si—OR and/or Si—OCOR groups, wherein R is typically a low molecular weight alkyl group;
(b) one or more polyalkyleneoxy groups comprising at least some ethyleneoxy units, said polyalkyleneoxy groups can be part of the polymer backbone, terminal groups (situated at the ends of the silicone polymer backbone), pendant groups, and mixtures thereof, with polyalkyleneoxy terminal and/or pendant groups being preferably capped with low molecular weight nonreactive capping groups, such as $C_1$–$C_6$ alkyl groups, but optionally can be reactive terminal groups, preferably in hindered or protected form that avoid excessive crosslinking prior to application; and (c) optionally but preferably one or more cationic nitrogen functional groups, being pendant groups, terminal groups, and/or part of the polymer backbone, and mixtures thereof, said cationic nitrogen functional group comprises, e.g., amine functional groups, imine functional groups, imidazole functional groups, imidazoline functional groups; quaternary ammonium functional groups, polycationic groups, and the like, and mixtures thereof.

Each reactive Si bearing a reactive functional group can be either a terminal group or within the silicone backbone. It can also optionally be on a pendant group. Each polyalkyleneoxy group can also be in various positions in the silicone polymer, including: (a) as pendant group linked to the silicone backbone by a linking group, preferably being a hydrocarbon or oxygenated hydrocarbon linking group, e.g., —CH$_2$CH$_2$CH$_2$—, —CH$_2$CH$_2$—, —CH$_2$CH(CH$_3$)CH$_2$—, —CH$_2$CH(OH)CH$_2$OCH$_2$CH$_2$—, -phenylene-CH$_2$CH$_2$—, and —CH$_2$-phenylene-CH$_2$CH$_2$—, or an aminoalkylene group, e.g., —CH$_2$CH$_2$CH$_2$—N< group and —CH$_2$CH(CH$_3$)CH$_2$—N< group, providing that no O—O or N—O bonds are formed; (b) as terminal group on the silicone, especially linked to the terminal Si atom by the same linking groups listed in (a) hereinabove; (c) as an internal group, incorporated into the main silicone chain by links selected from the linking groups listed in (a) hereinabove, providing that no O—O bonds are formed; and (d) mixtures thereof. Each optional cationic nitrogen functional group can also be in various positions in the silicone polymer, including: (a) as pendant group linked to the silicone backbone by a linking group, preferably being a hydrocarbon or oxygenated hydrocarbon linking group, e.g., —CH$_2$CH$_2$CH$_2$—, —CH$_2$CH$_2$—, —CH$_2$CH(CH$_3$)CH$_2$—, —CH$_2$CH(OH)CH$_2$OCH$_2$CH$_2$—, -phenylene-CH$_2$CH$_2$—, and —CH$_2$-phenylene-CH$_2$CH$_2$—, or an aminoalkylene group, e.g., —CH$_2$CH$_2$CH$_2$—N< group and —CH$_2$CH(CH$_3$)CH$_2$—N< group, providing that no N—N or N—O bonds are formed; (b) as terminal group on the silicone, especially linked to the terminal Si atom by the same groups listed in (a) above; (c) as an internal group, incorporated into the main silicone chain by links selected from the linking groups listed in (a) hereinabove and/or polyalkyleneoxy groups, providing that no N—N or N—O bonds are formed; (d) as terminal group on the end of a polyalkeneoxy terminal or pendant group, and linked to the polyalkeneoxy group through a hydrocarbon or oxygenated hydrocarbon linking group such as a —CH$_2$CH$_2$—, —CH(CH$_3$)CH$_2$— or —CH$_2$CH(OH)CH$_2$— group; and (e) mixtures thereof. The silicone polymer of the present invention can also preferably comprise at least two types of polyalkyleneoxy groups, selected from the group consisting of terminal group, pendant group, and/or internal polyalkyleneoxy group, and mixtures thereof. Similarly, the silicone polymer of the present invention can preferably comprise at least two types of optional cationic nitrogen groups, selected from the group consisting of pendant group, internal group, terminal group, and/or terminal group on the end of a polyalkeneoxy terminal or pendant group, and mixtures thereof.

The silicone polymers of the current invention conform to the following general structure:

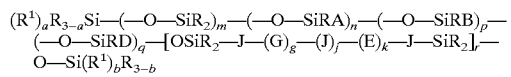

wherein:

each R group is the same or different and is preferably an alkyl, aryl, and mixtures thereof, more preferably, each R is methyl, ethyl, propyl, butyl, or phenyl group, most preferably R is methyl;

each A of the Si reactive functional group is the same or different and is preferably selected from the group consisting of hydrogen, —OH, —OR, —OCOCH$_3$, —CH$_2$CH$_2$Si(OR)$_3$, —CH$_2$CH$_2$Si(OR)$_2$R, —CH$_2$CH$_2$Si(OR)R$_2$, and mixtures thereof;

each optional, but preferred cationic B group is an —X—E group with each X being a hydrocarbon or oxygenated hydrocarbon linking group, preferably being selected from the group consisting of —CH$_2$CH$_2$CH$_2$—, —CH$_2$CH(CH$_3$)CH$_2$—, —CH$_2$CH$_2$—, —CH$_2$CH(OH)CH$_2$OCH$_2$CH$_2$CH$_2$—, and —CH$_2$-phenylene-CH$_2$CH$_2$—, and mixtures thereof; and each E being a cationic nitrogen functional group, preferably being selected from the group consisting of amino group and quaternary ammonium derivatives thereof; cyclic amino group and quaternary ammonium derivatives thereof; imidazole group and imidazolium derivatives thereof; imidazoline group and imidazolinium derivatives thereof; polycationic group, and mixtures thereof;

each optional D group is a poly(ethyleneoxy/propyleneoxy) group having the general structure:

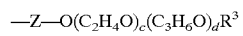

wherein each Z is a linking group, preferably selected from the group consisting of hydrocarbon or oxygenated hydrocarbon linking group, e.g., —CH$_2$CH$_2$CH$_2$—, —CH$_2$CH(CH$_3$)CH$_2$—, —CH$_2$CH$_2$—, —CH$_2$CH(OH)CH$_2$OCH$_2$CH$_2$CH$_2$—, -phenylene-CH$_2$CH$_2$— and —CH$_2$-phenylene-CH$_2$CH$_2$—; aminohydrocarbon linking group, e.g., —CH$_2$CH$_2$CH$_2$—N< group; —CH$_2$CH(CH$_3$)CH$_2$—N< group, and mixtures thereof; each R$^3$ group is the same or different and being preferably selected from the group consisting of hydrogen, R, JE, —CH$_2$CH(R)OH, —CH$_2$C(R)$_2$OH, —CH$_2$CH(OH)CH$_2$OR, —CH$_2$CH(OH)CH$_2$(OCH$_2$CH$_2$)$_e$OR, tetrahydropyranyl, —CH(R)OR, C(O)H, and/or —C(O)R group, more preferably R$^3$ group is an R group, with R being more preferably selected from methyl and/or ethyl group; each c is at least 2, preferably at least about 5, more preferably at least about 11, even more preferably at least about 21, total c (that is the sum of all of the ethyleneoxy units in the polymer, including all polyalkyleneoxy side groups) has a value of from about 4 to about 2500, preferably from about 6 to about 1000, more preferably from about 11 to about 800, and even more preferably from about 21 to about 500; total d is from 0 to about 1000, preferably from 0 to about 300; more preferably from 0 to about 100, and even more preferably d is 0; total c is preferably equal or larger than total d; total c+d has a value of from about 4 to about 2500, preferably from about 8 to about 800, and more preferably from about 15 to about 500; and each e is from 1 to about 20, preferably 1 or 2;

each optional G is —O(C$_2$H$_4$O)$_v$(C$_3$H$_6$O)$_w$—; each J is selected from X and —CH$_2$CH(OH)CH$_2$—; each optional E is a cationic group defined as hereinabove; each v is from 0 to about 200, preferably from about 5 to about 150, more preferably from about 11 to about 120, and even more preferably from about 20 to about 100; each w is from 0 to about 50 and preferably v is equal or larger than w; each g and k is from 0 to about 10, preferably from 0 to about 6, more preferably from about 1 to about 3, and even more preferably from about 1 to about 2; j is g+k−1, providing that no O—O bonds are formed;

each $R^1$ group is the same or different and is preferably selected from the group consisting of R, A, B, and/or D group;

each a and/or b is an integer from 0 to 3, preferably 2, more preferably 1;

m is from about 5 to about 1600, preferably from about 6 to about 800, more preferably from about 8 to about 400, and even more preferably from about 10 to about 200;

n, a, and b, and the $R^1$ groups of the terminal groups $(R^1)_a R_{3-a} Si$—O— and O—$Si(R^1)_b R_{3-b}$ are selected such that the silicone polymer comprises at least one reactive Si functional group in the form of an Si—A group, preferably Si—H, Si—OH, Si—OR, Si—OCOR, and mixtures thereof, with R preferably a methyl group; and more preferably the silicone molecule comprises at least about two reactive Si functional groups; with typically the n to (m+n) ratio (and the n to (m+n+p) ratio when p is not 0), ranges from 0 to about 1:2, preferably from about 1:1500 to about 1:3, more preferably from about 1:400 to about 1:4, and even more preferably from about 1:100 to about 1:4;

p, a, and b, and the $R^1$ groups of the terminal groups $(R^1)_a R_{3-a} Si$—O— and O—$Si(R^1)_b R_{3-b}$ are selected such that the silicone polymer optionally comprises at least one cationic group in the form of an Si—B group; with typically the p to (m+n+p) ratio ranges from 0 to about 1:2, preferably from about 1:200 to about 1:3, more preferably from about 1:100 to about 1:4, and even more preferably from about 1:50 to about 1:4; and q, a, and b, and the $R^1$ groups of the terminal groups $(R^1)_a R_{3-a} Si$—O— and O—$Si(R^1)_b R_{3-b}$ are selected such that the silicone polymer comprises at least one cationic poly(ethyleneoxy/propyleneoxy) Si—D group; and preferably at least about two Si—D groups; with typically the q to (m+n+p) ratio ranges from about 1:1000 to about 1:3, preferably from about 1:200 to about 1:4, more preferably from about 1:100 to about 1:4, and even more preferably from about 1:50 to about 1:5;

r is from 0 to about 100, and is preferably 0; when r is greater than 0, it is preferably from 1 to about 20, more preferably from 1 to about 10, with r being 0 when neither a polyalkyleneoxy group nor a cationic group is part of the polymer backbone; when one or more polyalkyleneoxy groups and/or cationic groups are part of the polymer backbone, the r to (m+n+p) ratio ranges typically from about 1:1000 to about 1:2, preferably from about 1:500 to about 1:4, more preferably from 1:200 to about 1:8, and even more preferably from about 1:100 to about 1:20;

wherein said silicone polymer can be linear, branched, and/or cyclic, preferably linear or branched, and more preferably linear; and wherein different —O—$SiR_2$—, —O—SiRA—, —O—SiRB—, —O—SiRD—, and —[$OSiR_2$—J—(G)$_g$—(J)$_j$—(E)$_k$—J—$SiR_2$]— groups can be distributed randomly in the silicone backbone and/or organized as block copolymers of different degrees.

The preferred hydrophilic curable silicones of the present invention comprise poly(alkyleneoxy) D groups, and preferably poly(ethyleneoxy) D groups that are exposed on the treated surface, and not being concealed and hidden within and/or underneath the silicone coating layer. This is achieved by (a) having the poly(ethyleneoxy) groups capped with a $C_1$–$C_4$ alkyl group, a hindered alcohol group, or a protected alcohol group, to prevent the poly(ethyleneoxy) groups from reacting with the reactive Si—A groups to become part of the backbone and/or cross-linking groups, and (b) not having the poly(ethyleneoxy) groups capped with cationic E groups if the poly(ethyleneoxy) groups are short, since cationic E groups are believed to have the tendency to anchor deep on the treated surface and thus also driving the poly(ethyleneoxy) groups deep underneath the silicone coating layer.

DETAILED DESCRIPTION OF THE INVENTION

The present invention relates to a class of novel curable silicone polymers comprising:

(a) one or more reactive Si functional groups including Si—H, Si—OH, Si—OR and/or Si—OCOR groups, wherein R is typically a low molecular weight alkyl group;

(b) one or more polyalkyleneoxy groups comprising at least some ethyleneoxy units, said polyalkyleneoxy groups can be part of the polymer backbone, terminal groups (situated at the ends of the silicone polymer backbone), pendant groups, and mixtures thereof, with polyalkyleneoxy terminal and/or pendant groups being preferably capped with low molecular weight nonreactive capping groups, such as $C_1$–$C_6$ alkyl groups, but optionally can be reactive terminal groups, preferably in hindered or protected form that avoid excessive crosslinking prior to application; and (c) optionally but preferably one or more cationic nitrogen functional groups, being pendant groups, terminal groups, and/or part of the polymer backbone, and mixtures thereof, said cationic nitrogen functional group comprises, e.g., amine functional groups, imine functional groups, imidazole functional groups, imidazoline functional groups; polycationic groups, quaternary ammonium functional groups, and the like, and mixtures thereof.

Each reactive Si bearing a reactive functional group can be either a terminal group or within the silicone backbone. It can also optionally be on a pendant group. Each polyalkyleneoxy group can also be in various positions in the silicone polymer, including: (a) as pendant group linked to the silicone backbone by a linking group, preferably being a hydrocarbon or oxygenated hydrocarbon linking group, e.g., —$CH_2CH_2CH_2$—, —$CH_2CH_2$—, —$CH_2CH(CH_3)CH_2$—, —$CH_2CH(OH)CH_2OCH_2CH_2CH_2$—, -phenylene-$CH_2CH_2$—, and —$CH_2$-phenylene-$CH_2CH_2$—, or an aminoalkylene group, e.g., —$CH_2CH_2CH_2$—N< group, providing that no O—O bonds are formed; (b) as terminal group on the silicone, especially linked to the terminal Si atom by the same linking groups listed in (a) hereinabove; (c) as internal group, incorporated into the main silicone chain by links selected from the linking groups listed in (a) hereinabove, providing that no O—O bonds are formed; and (d) mixtures thereof. Each optional cationic nitrogen functional group can also be in various positions in the silicone polymer, including: (a) as pendant group linked to the silicone backbone by a linking group, preferably being a hydrocarbon or oxygenated hydrocarbon linking group, e.g., —$CH_2CH_2CH_2$—, —$CH_2CH_2$—, —$CH_2CH(CH_3)CH_2$—, —$CH_2CH(OH)CH_2OCH_2CH_2CH_2$—, -phenylene-$CH_2CH_2$—, and —$CH_2$-phenylene-$CH_2CH_2$—, or an aminoalkylene group, e.g., —$CH_2CH_2CH_2$—N< group, providing that no N—N or N—O bonds are formed; (b) as terminal group on the silicone, especially linked to the terminal Si atom by the same groups listed in (a) above; (c) as internal group, incorporated into the main silicone chain by links selected from the linking groups listed in (a) hereinabove and/or polyalkyleneoxy groups, providing that no N—N or N—O bonds are formed; (d) as terminal group on the end of a polyalkeneoxy terminal or pendant group, especially linked to the polyalkeneoxy group through a hydrocarbon or oxygenated hydrocarbon linking group such as a —$CH_2CH_2$—, —$CH(CH_3)CH_2$— or —$CH_2CH(OH)CH_2$— group; and (e) mixtures thereof. The silicone polymer of the present invention can also preferably comprise at least two types of polyalkyleneoxy groups, selected from the group consisting of terminal group, pendant group, and/or internal polyalkyleneoxy group, and mixtures thereof. Similarly, the silicone polymer of the present invention can preferably comprise at least two types of optional cationic nitrogen groups, selected from the group consisting of pendant group, internal group, terminal group, terminal group on the end of a polyalkeneoxy terminal or pendant group, and mixtures thereof.

The silicone polymers of the current invention conform to the following general structure:

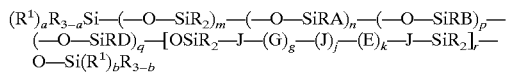

wherein:
   each R group is the same or different and is preferably an alkyl, aryl, and mixtures thereof, more preferably, each R is methyl, ethyl, propyl, butyl, or phenyl group, most preferably R is methyl;
   each A of the Si reactive functional group is the same or different and is preferably selected from the group consisting of hydrogen, —OH, —OR, —$OCOCH_3$, —$CH_2CH_2Si(OR)_3$, —$CH_2CH_2Si(OR)_2R$, —$CH_2CH_2Si(OR)R_2$, and mixtures thereof;
   each optional, but preferred cationic B group is an —X—E group with each X being a hydrocarbon or oxygenated hydrocarbon linking group, preferably being selected from the group consisting of —$CH_2CH_2CH_2$—, —$CH_2CH(CH_3)CH_2$—, —$CH_2CH_2$—, —$CH_2CH(OH)CH_2OCH_2CH_2CH_2$—, and —$CH_2$-phenylene-$CH_2CH_2$—, and mixtures thereof; and each E being a cationic nitrogen functional group, preferably being selected from the group consisting of amino group and quaternary ammonium derivatives thereof; cyclic amino group and quaternary ammonium derivatives thereof; imidazole group and imidazolium derivatives thereof; imidazoline group and imidazolinium derivatives thereof; polycationic group; and mixtures thereof;
   each optional D group is a poly(ethyleneoxy/propyleneoxy) group having the general structure:

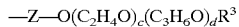

wherein each Z is a linking group, preferably selected from the group consisting of hydrocarbon or oxygenated hydrocarbon linking group, e.g., —$CH_2CH_2CH_2$—, —$CH_2CH(CH_3)CH_2$—, —$CH_2CH_2$—, —$CH_2CH(OH)CH_2OCH_2CH_2CH_2$—, -phenylene-$CH_2CH_2$— and —$CH_2$-phenylene-$CH_2CH_2$—; aminohydrocarbon linking group, e.g., —$CH_2CH_2CH_2$—N< group and —$CH_2CH(CH_3)CH_2$—N< group; and mixtures thereof; each $R^3$ group is the same or different and being preferably selected from the group consisting of hydrogen, R, cationic nitrogen functional E group, —$CH_2CH(R)OH$, —$CH_2C(R)_2OH$, —$CH_2CH(OH)CH_2OR$, —$CH_2CH(OH)CH_2(OCH_2CH_2)_eOR$, tetrahydropyranyl, —CH(R)OR, C(O)H, and/or —C(O)R group, more preferably $R^3$ group is an R group, with R being more preferably selected from methyl and/or ethyl group; each c is at least about 2, preferably at least about 5, more preferably at least about 11, and even more preferably at least about 21, total c (for all polyalkyleneoxy side groups) has a value of from about 4 to about 2500, preferably from about 6 to about 1000, more preferably from about 11 to about 800, and even more preferably from about 21 to about 500; total d is from 0 to about 1000, preferably from 0 to about 300; more preferably from 0 to about 100, and even more preferably d is 0; preferably total c is equal or larger than total d; total c+d has a value of from about 4 to about 2500, preferably from about 8 to about 800, and more preferably from about 15 to about 500; and each e is from 1 to about 20, preferably 1 or 2;
   each optional G is —$O(C_2H_4O)_v(C_3H_6O)_w$—; each J is selected from X and —$CH_2CH(OH)CH_2$—; each optional E is a cationic group defined as hereinabove; each v is from 0 to about 200, preferably from about 5 to about 150, more preferably from about 11 to about 120, and even more preferably from about 21 to about 100; each w is from 0 to about 50 and preferably v is equal or larger than w; each g and k is from 0 to about 10, preferably from 0 to about 6, more preferably from about 1 to about 3, and even more preferably from about 1 to about 2; j is g+k−1, within the segment designated as $(G)_g$—$(J)_j$—$(E)_k$, the units can be arranged in any order, providing that no O—O bonds and/or N—N are formed;
   each $R^1$ group is the same or different and is preferably selected from the group consisting of R, A, B, and/or D group;
   each a and/or b is an integer from 0 to 3, preferably 2, more preferably 1;
   m is from about 5 to about 1600, preferably from about 6 to about 800, more preferably from about 8 to about 400, and even more preferably from about 10 to about 200;
   n, a, and b, and the $R^1$ groups of the terminal groups $(R^1)_aR_{3-a}Si$—O— and O—$Si(R^1)_bR_{3-b}$ are selected such that the silicone molecule comprises at least one reactive Si functional group in the form of an Si—A group, preferably Si—H, Si—OH, Si—OR, Si—OCOR, and mixtures thereof, with R preferably a methyl group; and more preferably the silicone polymer comprises at least about two reactive Si functional groups; with typically the n to (m+n) ratio (and the n to (m+n+p) ratio when p is not 0), ranges from 0 to about 1:2, preferably from about 1:1500 to about 1:3, more preferably from about 1:400 to about 1:4, and even more preferably from about 1:100 to about 1:4;
   p, a, and b, and the $R^1$ groups of the terminal groups $(R^1)_aR_{3-a}Si$—O— and O—$Si(R^1)_bR_{3-b}$ are selected such that the silicone polymer optionally comprises at least one cationic group in the form of an Si—B group; with typically the p to (m+n+p) ratio ranges from 0 to about 1:2, preferably from about 1:200 to about 1:3, more preferably from about 1:100 to about 1:4, and even more preferably from about 1:50 to about 1:4; and
   q, a, and b, and the $R^1$ groups of the terminal groups $(R^1)_aR_{3-a}Si$—O— and O—$Si(R^1)_bR_{3-b}$ are selected such that the silicone polymer comprises at least one poly(ethyleneoxy/propyleneoxy) Si—D group; and preferably at least about two Si—D groups; with typically the q to (m+n+p+q) ratio ranges from about 1:1000 to about 1:3, preferably from about 1:200 to about 1:4, more preferably from about 1:100 to about 1:4, and even more preferably from about 1:50 to about 1:5;

r is from 0 to about 100, and is preferably 0; when r is greater than 0, it is preferably from 1 to about 20, more preferably from 1 to about 10, with r being 0 when neither a polyalkyleneoxy group nor a cationic group is part of the polymer backbone; when one or more polyalkyleneoxy groups and/or cationic groups are part of the polymer backbone, the r to (m+n+p) ratio ranges typically from about 1:1000 to about 1:2, preferably from about 1:500 to about 1:4, more preferably from 1:200 to about 1:8, and even more preferably from about 1:100 to about 1:20;

wherein said silicone polymer can be linear, branched, and/or cyclic, preferably linear or branched, and more preferably linear; and wherein different —O—SiR$_2$—, —O—SiRA—, —O—SiRB—, —O—SiRD—, and —[OSiR$_2$—J—(G)$_g$—(J)$_j$—(E)$_k$—J—SiR$_2$]— groups can be distributed randomly in the silicone backbone and/or organized as block copolymers of different degrees.

The preferred hydrophilic curable silicones of the present invention comprise poly(alkyleneoxy) D groups, and preferably said poly(ethyleneoxy) D groups are exposed on the treated surface, and not being concealed and hidden within and/or underneath the silicone coating layer, in order to provide the surface hydrophilicity. This is achieved by (a) having the poly(ethyleneoxy) groups capped with a $C_1$–$C_4$ alkyl group, a hindered alcohol group, or a protected alcohol group, to prevent the poly(ethyleneoxy) groups from reacting with the reactive Si—A groups to become part of the backbone and/or cross-linking groups, and (b) not having the poly(ethyleneoxy) groups capped with cationic E groups if the poly(ethyleneoxy) groups are short, since cationic E groups are believed to have the tendency to anchor deep on the treated surface and thus also driving the poly (ethyleneoxy) groups deep underneath the silicone coating layer. To improve hydrophilicity property, each capping cationic group E, if present, is preferably small, comprising less than about 10 carbon atoms, preferably less than about 8 carbon atoms, more preferably less than about 7 carbon atoms, and even more preferably less than about 6 carbon atoms. To effectively avoid crosslinking or reduce the crosslinking by the poly(alkyleneoxy) D groups, any capping alcohol group needs to have the OH group well protected; therefore tertiary alcohol groups such as —CH$_2$C(R$_2$)OH or hindered secondary alcohol groups, such as —CH$_2$CH(R$^4$)(OH), with R$^4$ not being H or CH$_3$, are preferred. If the capping alcohol groups are not hindered, but readily available, then they can condense with the reactive silicone groups to cause excessive crosslinking resulting in a silicone that can not be solubilized and/or dispersed in the compositions of the present invention.

However, it will be appreciated that large poly(ethylene oxide) groups are less needful of these capping group restrictions, since they are less likely to be completely covered by the silicone segments in the cured layer. Thus, the present invention also relates to hydrophilic curable silicones with uncapped pendant poly(alkyleneoxy) D groups (i.e., poly(alkyleneoxy) D groups terminated by a —OH) and/or capped with cationic E groups to increase crosslinking and/or surface substantivity, wherein each pendant poly(alkyleneoxy) D group preferably comprises at least about 11 ethyleneoxy units (i.e., c being equal or greater than about 11), more preferably at least about 15 ethyleneoxy units (c being equal or greater than about 15), more preferably at least about 21 ethyleneoxy units (c being equal or greater than about 21), and more preferably at least about 30 ethyleneoxy units (c being equal or greater than about 30). Similarly, when internal poly(ethyleneoxy) G groups which form part of the polymer backbone are desirable, each G group should preferably comprise at least about 11 ethyleneoxy units (i.e., v being equal or greater than about 11), more preferably at least about 15 ethyleneoxy units (v being equal or greater than about 15), more preferably at least about 21 ethyleneoxy units (c being equal or greater than about 21), and more preferably at least about 30 ethyleneoxy units (v being equal or greater than about 30).

Silicones of the type

$$[A_bR(C_nH_{2n}O)_xCH_2\text{—}CH(OC_nH_{2n})_xRA_c\text{—}CH_2(OC_nH_{2n})_xRA_d]_a$$

as disclosed in U.S. Pat. No. 4,246,423 issued Jan. 20, 1981 to E. R. Martin, are not part of the present invention because they are claimed to impart hydrophobic property to fabrics; said patent is incorporated herein by reference.

The present invention also relates to the use of the hydrophilic curable silicone polymers of the present invention to treat fabric to provide at least one of the following long lasting fabric care benefits: wrinkle control, wrinkle resistance, fabric wear reduction, fabric wear resistance, fabric pilling reduction, fabric color maintenance, fabric color fading reduction, fabric color restoration, fabric softness, fabric soiling reduction, fabric soil release, fabric shape retention, ease of ironing, fabric comfort, fabric hydrophilicity, static control, and/or fabric shrinkage reduction.

The hydrophilic curable silicone polymers of the present invention can be formulated as aqueous compositions, such as solutions, emulsions, and/or dispersions. However, since these silicone polymers have reactive functional groups that can condense to form Si—O—Si bonds in the presence of moisture, it is also preferred to formulate said silicone polymers in anhydrous compositions for long term stability. Examples of preferred compositions are gels, waxes, powders, and anhydrous liquid compositions comprising anhydrous solvents that do not promote crosslinking, such as monohydric alcohols. When a dilute aqueous composition is desirable, it is best to first prepare a concentrated composition containing the desired curable silicone in a suitable anhydrous solvent which is miscible with water, such as anhydrous low molecular weight alcohols, e.g., ethanol, methanol, isopropanol, and mixtures thereof, such a concentrated composition is then diluted with water immediately prior to to the target surface, and then let dry and cure on the surface. Because of this complex procedure, it is preferred to provide the hydrophilic curable silicone polymers of the present invention to the consumer in the form of an article of manufacture comprising an anhydrous composition in association with instructions for use to direct the consumer to properly apply an effective amount of hydrophilic curable silicone polymer to the surface to provide the desired benefits.

For fabric care, the composition of the present invention can be applied to fabric and/or an entire garment via a, e.g., dipping, soaking, misting and/or spraying process, followed by a drying step. The application can be done industrially by large scale processes on textiles and/or finished garments and clothing, or in a consumer's home by the use of a commercial product. For a fabric care consumer spray product, it is desirable that the spraying and/or misting of the entire garment occurs in a manner such that excessive amounts of the fabric/garment care composition are prevented from being released to the open environment. For example, the spraying and/or misting of the entire garment is done in an enclosed and/or containable space, such as within a bag, a cabinet, or other articles suitable for containing the garment.

The curable silicones of the present invention can also be formulated with or used in conjunction with other reactive silicones or silanes as co-reactants in the curing process. For example, silicones of the present invention can be used with 3-aminopropyltrimethoxysilane, 3-aminopropylmethyldimethoxysilane, tetraethoxysilane, diacetoxymethyl terminated polydimethylsiloxanes, and the like and mixtures thereof.

The present invention also relates to hydrophilic nonreactive, noncurable cationic silicone polymers comprising cationic amino functional groups and hydrophilic polyalkyleneoxy groups. They have a similar structure as the general structure given hereinabove, with n being 0, and with $R^1$ groups not comprising A groups. These noncurable cationic slicone polymers can provide an intermediate durability benefit which is preferred in some applications. Said noncurable cationic slicone polymers preferably comprise poly(ethyleneoxy) D pendant and/or terminal groups that are exposed on the treated surface, and not being concealed and hidden within and/or underneath the silicone coating layer. This is achieved by (a) having the poly(ethyleneoxy) pendant groups not capped with cationic functional capping groups, (b) when cationic functional groups are needed on the poly(ethyleneoxy) pendant groups, e.g., for improved surface substantivity, each pendant poly(alkyleneoxy) D group should comprise at least about 11 ethyleneoxy units (i.e., c being equal or greater than about 11), more preferably at least about 15 ethyleneoxy units (c being equal or greater than about 15), more preferably at least about 21 ethyleneoxy units (c being equal or greater than about 21), and even more preferably at least about 30 ethyleneoxy units (c being equal or greater than about 30), and/or (c) when internal poly(ethyleneoxy) G groups which form part of the polymer backbone are present, each G group should preferably comprise at least about 11 ethyleneoxy units (i.e., v being equal or greater than about 11), more preferably at least about 15 ethyleneoxy units (v being equal or greater than about 15), more preferably at least about 15 ethyleneoxy units (c being equal or greater than about 15), and even more preferably at least about 30 ethyleneoxy units (v being equal or greater than 30).

In this case where there are no reactive Si functions A, and where there are quaternary nitrogen moieties E, in the backbone or on the ends of the backbone (with k>0 and/or $R^3$ being JE) and where there are no pendant cationic groups (p=0), then J shall not comprise groups consisting of ring-opened epoxides. That is, in this special case, J will be selected only from hydrocarbon links, preferably the group consisting of —CH$_2$CH$_2$CH$_2$—, —CH$_2$CH$_2$—, and —CH$_2$-phenylene-CH$_2$CH$_2$—, and mixtures thereof.

The silicones of the present inventions can preferably comprise polyalkyleneoxy groups as terminal groups, pendant groups, backbone groups (forming part of the polymer backbone), and mixtures thereof.

The present invention also relates to the use of the silicone polymers of the present invention to treat fabric, to provide at least one of the following fabric care benefits: wrinkle control, wrinkle resistance, fabric wear reduction, fabric wear resistance, fabric pilling reduction, fabric color maintenance, fabric color fading reduction, fabric color restoration, fabric softness, fabric soiling reduction, fabric soil release (both oily and particulate soils), fabric shape retention, ease of ironing, fabric comfort, static control, fabric hydrophilicity, and/or fabric shrinkage reduction. The silicone polymers of the present invention can provide at least some fabric care benefits to all types of fabrics, including fabrics made of natural fibers, synthetic fibers, and mixtures thereof. Nonlimiting examples of fabric types that can be treated with the fabric care compositions of the present invention, to obtain fabric care benefits include fabrics made of (1) cellulosic fibers such as cotton, rayon, linen, Tencel, (2) proteinaceous fibers such as silk, wool and related mammalian fibers, (3) synthetic fibers such as polyester, acrylic, nylon, and the like, (4) long vegetable fibers from jute, flax, ramie, coir, kapok, sisal, henequen, abaca, hemp and sunn, and (5) mixtures thereof.

The present invention also relates to a method for providing a fabric with a fabric care benefit selected from the group consisting of: wrinkle control, wrinkle resistance, fabric wear reduction, fabric wear resistance, fabric pilling reduction, fabric color maintenance, fabric color fading reduction, fabric color restoration, fabric softness, fabric soiling reduction, fabric soil release, fabric shape retention, ease of ironing, fabric comfort, fabric hydrophilicity, static control, and/or fabric shrinkage reduction, wherein said method comprises contacting said fabric with an effective amount silicone polymers of the present invention to provide a noticeable benefit. In a preferred method, said silicone polymers are provided by using anhydrous compositions or freshly prepared aqueous compositions as described hereinabove. The present invention further relates to the use of the silicone polymers of the present invention to treat fabric, to provide at least one of the following fabric care benefits: wrinkle control, wrinkle resistance, fabric wear reduction, fabric wear resistance, fabric pilling reduction, fabric color maintenance, fabric color fading reduction, fabric color restoration, fabric softness, fabric soiling reduction, fabric soil release, fabric shape retention, ease of ironing, fabric comfort, fabric hydrophilicity, static control, and/or fabric shrinkage reduction. The silicone polymers, compositions, methods, and articles of manufacture comprising said polymers, can provide the benefits hereinabove to both consumer, household fabrics such as clothings, bed linens, curtains, drapes, and the like, and industrial, institutional, and/or commercial fabrics such as uniforms, bed linens, tablecloths, and the like.

Hydrophilic Curable Silicones

Following are nonlimiting examples of hydrophilic curable silicones of the present invention. These materials are prepared from intermediate materials that can be prepared as follows:

Alkoxylated Allyl Alcohols

Ethoxylated(5) Allyl Alcohol, Intermediate Material A To a 250 ml, three neck, round bottom flask equipped with a magnetic stirring bar, condenser, thermometer, and temperature controller (Therm-O-Watch®, I$^2$R) is added allyl alcohol (Aldrich, about 24.5 g, about 0.422 mol, from Aldrich, Milwaukee, Wis.) under argon. Sodium metal (Aldrich, about 0.78 g, about 0.034 mol) is added in three increments. An exotherm occurs (about 60° C.), and after the sodium is dissolved, the solution is heated to about 80° C. Ethylene oxide gas is added via a sparging tube with rapid stirring. The temperature of the system is kept below about 130° C. during the addition of ethylene oxide, which is stopped when a weight gain of about 77.3 g, corresponding to about 4.2 ethoxy units, is obtained. A $^1$H-NMR(CDCl$_3$) shows resonances for the allyl peaks at ~5.9 ppm (CH$_2$=C$\underline{H}$—), ~5.2 ppm (C$\underline{H}_2$=CH—), and ~4 ppm (CH$_2$=CHC$\underline{H}_2$—), and a large resonance for the hydrogens from the ethoxy groups at ~3.5–3.8 ppm. Integration of these peaks indicates that the degree of ethoxylation is about 5. The material is neutralized to about pH 7 with methanesulfonic acid (Aldrich). The resulting salt is removed by gravity filtration of the neat material.

Ethoxylated(10) Allyl Alcohol, Intermediate Material B. The preparation used to prepare Intermediate Material A is repeated except that it is conducted in a stirred autoclave and the total ethylene oxide condensed is increased to give the desired $H(OCH_2CH_2)_nOCH_2CH=CH_2$ with average n of about 10.

Ethoxylated (24) Allyl Alcohol, Intermediate Material B1. The preparation used to prepare Intermediate Material A is repeated except that the total ethylene oxide condensed is increased to give the desired $H(OCH_2CH_2)_nOCH_2CH=CH_2$ with average n of about 24.

Alkoxylated Allyl Alcohol, Intermediate Material C. The preparation used to prepare Intermediate Material A is repeated in the autoclave except that propylene oxide is first condensed with the allyl alcohol and when an average of about 3 units have been condensed, ethylene oxide is condensed until a total average of about 3 propylene oxides and about 7 ethylene oxides have been condensed per allyl alcohol to give the desired final mixed alkoxylate, $H(OCH_2CH_2)_n(OCH(CH_3)CH_2)_mOCH_2CH=CH_2$ with average n of about 7 and average m of about 3.

Ethoxylated Allyl Amines

Allyldiethanolamine, Intermediate Material D. Allyl amine (about 228 g, about 4.0 mol, Aldrich) is placed in a 2 liter, stirred autoclave and is heated to about 100° C. under about 200 psi pressure of nitrogen gas. Ethylene oxide (about 352 g, about 8.0 mol, Balchem Corp., State Hill, N.Y.) is gradually pumped into the system with care to keep the temperature in the 90–110° C. range. After the pressure stabilizes, the autoclave is cooled to room temperature and depressurized. Then, about 435 g of the resulting hydroxyethylated amine (allyldiethanolamine) is removed from the autoclave.

Ethoxylated Allyl Amine, Intermediate Material E. The approximate 145 g (about 1 mol) of allyldiethanolamine D remaining in the autoclave is treated with about 21.6 g (about 0.1 mol) of 25% sodium methoxide in methanol (Aldrich) and the methanol is removed from the system by stirring and applying vacuum and gradually raising the temperature to about 100° C. After the methanol is removed, ethylene oxide is added gradually, keeping the temperature in the 100–110° C. range. Addition is continued until a total of about 8 moles of ethylene oxide has been added during the base catalyzed phase of the ethoxylation. After the pressure stabilizes, the system is cooled to about 50° C. and about 248 g (about 0.5 mol) of ethoxylated allylamine is withdrawn and the strong base is neutralized by adding about 0.05 moles of methanesulfonic acid to give the desired product, $CH_2=CHCH_2N[(CH_2CH_2O)_nH]_2$ with average n of about 5.

Ethoxylated Allyl Amine, Intermediate Material F. About 0.5 moles of the ethoxylated product E remaining in the autoclave is again raised to about 100° C. and about 220 g (about 5 mol.) ethylene oxide is condensed under the same conditions used previously. After the pressure stabilizes, the autoclave is cooled and about 234 g of the product is removed and neutralized as before to give the desired product, $CH_2=CHCH_2N[(CH_2CH_2O)_nH]_2$ with average n of about 10.

Ethoxylated Allyl Amine, Intermediate Material F1. About 0.25 moles of the ethoxylated product remaining in the autoclave is again raised to about 100° C. and about 264 g (about 6 mol.) ethylene oxide is condensed under the same conditions used previously. After the pressure stabilizes, the autoclave is cooled and the product is removed and neutralized as before to give the desired product, $CH_2=CHCH_2N[(CH_2CH_2O)_nH]_2$ with average n of about 22.

Etherification of Ethoxylated Allyl Amine

Methyl Capped Ethoxylated Allyl Amine, Intermediate Material G. Ethoxylation of allylamine is conducted as described in the above example to prepare a sample of about 497 g (about 1 mol.) $CH_2=CHCH_2N[(CH_2CH_2O)_nH]_2$ with average n=5 (Intermediate Material E). However, in this case, the ethoxylated reaction product is not removed from the autoclave, but is further treated with about 216 g (about 1.0 mol) of 25% sodium methoxide in methanol and then the methanol is completely stripped from the autoclave by applying vacuum and raising the temperature gradually to about 100° C. with good stirring. After all the methanol is removed, the reaction mixture is cooled to room temperature and about 500 ml of tetrahydrofuran is added, followed by gradually adding about 50.5 g (about 1.0 mol.) chloromethane (Aldrich). The reaction mixture is stirred vigorously and after the initial exotherm, the temperature is raised and held at about 60° C. for one hour. Then an additional about 1.0 moles of sodium methoxide is added and the methanol and tetrahydrofuran are removed under vacuum as before. Tetrahydrofuran is again added as a solvent and another about 50.5 g (about 1.0 mol.) of chloromethane is added as before and allowed to react. After the chloromethane has reacted, the reaction mixture is removed from the autoclave and salts are removed by filtration. The tetrahydrofuran is removed by stripping under vacuum to yield an oil from which a small amount of additional salt is removed by filtration to give the desired methyl capped, ethoxylated allylamine, $CH_2=CHCH_2N[(CH_2CH_2O)_nCH_3]_2$ with average n of about 5.

Methyl Capped Ethoxylated Allyl Amine, Intermediate Materials G1 and G2. The process is repeated with the more highly ethoxylated samples F and F1 of allylamine prepared earlier to give the desired capped materials, $CH_2=CHCH_2N[(CH_2CH_2O)_nCH_3]_2$, with average n of about 10 and 22, respectively.

Hydroxyisobutyl Capped Ethoxylated Allylamine, Intermediate Material H. Ethoxylation of allylamine is repeated as described above, but after the ethoxylation has reached a degree of about 10, the $CH_2=CHCH_2N[(CH_2CH_2O)_nH]_2$ (n=about 10, Intermediate Material F) in the autoclave still containing strong alkaline catalyst, is further treated with two moles of isobutene oxide (BASF) for each mole of ethoxylated intermediate. Heating is continued at about 100–110° C. until all the isobutene oxide is consumed and the reaction mixture is then cooled and removed from the reactor and the strong base catalyst is neutralized by adding methanesulfonic acid. This produces the desired ethoxylated allylamine with hindered alcohol termini, $CH_2=CHCH_2N[(CH_2CH_2O)_n-CH_2C(OH)(CH_3)_2]_2$ with average n of about 10.

Ethoxylated Allylamine with Hindered Alcohol Capping Group Derived from a Glycidyl Ether, Intermediate H1.

Ethoxylation of allylamine is repeated as described above, but after the ethoxylation has reached a degree of about 10, the $CH_2=CHCH_2N[(CH_2CH_2O)_nH]_2$ (n=about 10, Intermediate Material F) in the autoclave still containing strong alkaline catalyst, is further treated with two moles of glycidyl methyl ether for each mole of ethoxylated intermediate. Heating is continued at about 100–110° C. until all the glycidyl methyl ether is consumed and the reaction mixture is then cooled and removed from the reactor and the strong base catalyst is neutralized by adding methanesulfonic acid. This produces the desired ethoxylated allylamine with hindered alcohol termini, $CH_2=CHCH_2N[(CH_2CH_2O)_n-CH_2C(OH)CH_2OCH_3]_2$ with average n of about 10.

Ether Capping of Alkoxylated Allyl Alcohol

Methyl Capped Ethoxylated Allyl Alcohol, Intermediate Material J. A portion of about 27.8 g (about 0.1 mole) of allyl alcohol with degree of ethoxylation equal to about 5 (Intermediate Material A) is dissolved in about 200 ml of tetrahydrofuran in a 500 ml round bottom flask equipped with magnetic stirring, condenser and set up for blanketing with argon. Sodium hydride (about 2.7 g, about 0.11 mol.) is added in portions to the stirred reaction mixture and after the initial exotherm, mild heating to about 50° C. is continued until gas evolution stops. The reaction mixture is cooled to about 10° C. and the condenser is replaced by a solid $CO_2$ condenser. Then, gaseous methyl bromide is passed into the reaction mixture until an excess is present and the reaction mixture is stirred and the temperature is allowed to rise to near room temperature. After about 4 hours, the reaction mixture is filtered and then the solvent is removed under vacuum on a rotary evaporator to leave the desired methyl ether of ethoxylated allyl alcohol, $CH_3(OCH_2CH_2)_nOCH_2CH=CH_2$ with average n of about 5.

Methyl Capped Ethoxylated Allyl Alcohol, Intermediate Material J1 and J2. The same procedure is repeated with the more highly ethoxylated allyl alcohols prepared as described (Intermediates B and B1) to give additional samples of $CH_3(OCH_2CH_2)_nOCH_2CH=CH_2$ with average n of about 10 and 24, respectively.

Methyl Capped Alkoxylated Allyl Alcohol, Intermediate J3. The same procedure is applied to Intermediate Material C to obtain the corresponding methyl ether of the mixed propoxylated-ethoxylated allyl alcohol.

Hindered Alcohol-Capped Ethoxylated Allyl Alcohol, Intermediate J4. Allyl alcohol is ethoxylated in an autoclave as previously described to an ethoxylation degree of about 20. Prior to neutralizing the basic catalyst, the ethoxylated material is further treated with 1 mole of isobutene oxide (BASF) for each mole of ethoxylated intermediate. Heating is continued at about 100–110° C. until all the isobutene oxide is consumed and the reaction mixture is then cooled and removed from the reactor and the strong base catalyst is neutralized by adding methanesulfonic acid. This produces the desired ethoxylated(20) allyl alcohol capped with a $-CH_2C(CH_3)_2(OH)$ group.

Tetrahydropyranyl Ether of Ethoxylated Allyl Alcohol

Tetrahydropyranyl Ether of Ethoxylated Allyl Alcohol, Intermediate Material K. A portion of about 27.8 g (about 0.1 mole) of allyl alcohol with degree of ethoxylation equal to about 5 (Intermediate Material A) is dissolved in about 50 ml of methylene chloride in a 250 ml round bottom flask equipped with magnetic stirring, condenser and set up for blanketing with argon. Then, 3,4-dihydro-2H-pyran (about 16.8 g, about 0.2 mol, Aldrich) is added along with about 0.1 g p-toluenesulfonic acid monohydrate (Aldrich) and the system is allowed to stir at room temperature for about 6 hours. The acid catalyst is neutralized by adding a small excess of base in the form of about 0.15 g of 25% sodium methoxide in methanol (Aldrich) and the solvent and excess dihydropyran are stripped off on the rotary evaporator and salts are removed by filtration to yield the desired tetrahydropyranyl ether, $THP-(OCH_2CH_2)_nOCH_2CH=CH_2$ with average n of about 5.

Intermediate Material K1 and K2. The preparation of Intermediate Material K is repeated except that ethoxylated allyl alcohols with degree of ethoxylation of about 10 and 24 (Intermediate Materials B and B1) are used to give the desired tetrahydropyranyl ethers of ethoxylated (10) allyl alcohol and ethoxylated (24) allyl alcohol, Intermediate Materials K1 and K2.

Allyl Ether of Imidazole Ethoxylate

Intermediate Material M. Allyl alcohol is ethoxylated using basic catalysis to a degree of about 10. A portion of about 49.8 g (about 0.10 mol) of the resulting allyl ethoxylate is placed in a 250 ml round bottom flask equipped with reflux condenser, dropping funnel, magnetic stirring and argon blanketing, and about 1 g of N,N-dimethylformamide (Aldrich) is added. Then the reaction mixture is heated to about 70° C. with vigorous stirring as about 14.3 g (about 0.12 mol) thionyl chloride is added dropwise over about one hour. Heating is continued for about 18 hours and the excess thionyl chloride is removed by stripping on a rotary evaporator. The resulting oil is then added with vigorous stirring to a 500 ml round bottom flask containing about 80 g (about 1.0 mol) of imidazole and the reaction mixture is heated to about 80° C. and held there for about 18 hours. The reaction mixture is cooled and about 21.6 g (about 0.1 mole) of about 25% sodium methoxide in methanol is added and then the methanol and excess imidazole are stripped off on the rotary evaporator and the kugelrohr to give an oil with a salt precipitate. The salt is removed by filtration to yield the imidazole-terminated allyl ethoxylate, $CH_2=CHCH_2(OCH_2CH_2)_n$-imidazole where average n is about 10.

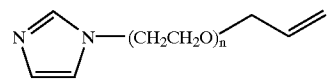

Hydrosilation of Ethers of Ethoxylated Allyl Alcohol with Alkoxysilanes

Intermediate Hydrosilation Material N. A portion of about 29.2 g (about 0.1 mol.) of $CH_3(OCH_2CH_2)_nOCH_2CH=CH_2$ with average n of about 5 (Intermediate Material J) is placed in a 250 ml round bottom flask equipped with magnetic stirring, distillation head, dropping funnel, and argon blanketing and about 125 ml of toluene is added. The solution is brought to a boil and about 25 ml of toluene is distilled out along with traces of moisture. The distillation head is replaced with a reflux condenser, about 0.1 g (about 0.00024 mol.) chloroplatinic acid (Aldrich) is added, and the solution is brought to reflux. Then about 20 g triethoxysilane (about 0.12 mol, Aldrich) is added dropwise over about 30 minutes and the reflux is continued for about 4 hours. The reaction mixture is cooled and the solvent and excess silane are stripped on a rotary evaporator to give the desired hydrosilated product, $CH_3(OCH_2CH_2)_nOCH_2CH_2CH_2Si(OCH_2CH_3)_3$ with n of about 5.

Intermediate Hydrosilation Material N1. The procedure for preparing Intermediate Material N is repeated except methyldiethoxysilane is substituted for the triethoxysilane. This yields the desired diethoxysilane, $CH_3(OCH_2CH_2)_nOCH_2CH_2CH_2Si(CH_3)(OCH_2CH_3)_2$ with average n of about 5.

Hydrosilation of Ethers of Ethoxylated Allyl Alcohol with Cyclic Hydrosiloxanes

Intermediate Hydrosilation Material O. A portion of about 51 g (about 0.1 mol.) portion of $CH_3(OCH_2CH_2)_nOCH_2CH=CH_2$ with n of about 10, prepared as above (Intermediate Material J1) is placed in a 250 ml. Round bottom flask equipped with magnetic stirrer, argon blanketing, and a distillation head. A portion of about 100 ml. of toluene is added and about 25 ml. of toluene are distilled off to dry the system. The distillation head is replaced by a reflux condenser. A portion of about 6 g (about 0.025 mol.) of 1,3,5,7-tetramethylcyclotetrasiloxane (Gelest Inc., Tullytown, Pa., is added along with about a 20 μL portion of platinum-divinyltetramethyldisiloxane complex in xylene (Gelest), and the reaction mixture is heated to reflux for about 5 hours. After reflux, an aliquot shows an NMR spectrum that indicates substantially all the allyl groups have reacted. The solvent is stripped off to yield the desired ethoxylate-substituted cyclotetrasiloxane, [Si(O)(CH$_3$)CH$_2$CH$_2$CH$_2$(OCH$_2$CH$_2$)$_{10}$OCH$_3$]$_4$.

Intermediate Hydrosilation Material P. The synthesis of Intermediate Material O is repeated except that the methyl capped ether is replaced by the tetrahydropyranyl-capped ether, THP—(OCH$_2$CH$_2$)$_n$OCH$_2$CH=CH$_2$ (Intermediate Material K1) with average n of about 10, prepared as above. A portion of about 0.5 g of triethylamine is also added to ensure that the system remains slightly alkaline. This yields the desired THP-capped ethoxylate-substituted cyclotetrasiloxane, [Si(O)(CH$_3$)CH$_2$CH$_2$CH$_2$(OCH$_2$CH$_2$)$_{10}$O—THP]$_4$.

Intermediate Hydrosilation Material P1. The synthesis is repeated, except that more highly ethoxylated THP ether (Intermediate Materials K2), is used to obtained the desired cyclotetrasiloxane [Si(O)(CH$_3$)CH$_2$CH$_2$CH$_2$(OCH$_2$CH$_2$)$_{24}$O—THP]$_4$.

Hydrosilation of Ethers of Ethoxylated Allylamine with Cyclic Hydrosiloxanes

Intermediate Hydrosilation Material Q. A portion of about 52.5 g (about 0.1 mol.) of CH$_2$=CHCH$_2$N[(CH$_2$CH$_2$O)$_n$CH$_3$]$_2$ with average n of about 5, prepared as above (Intermediate Material G) is placed in a 250 ml. Round bottom flask equipped with magnetic stirrer, argon blanketing, and a distillation head. A portion of about 100 ml. of toluene is added and about 25 ml. of toluene is distilled off to dry the system. The distillation head is replaced by a reflux condenser. A portion of about 6 g (about 0.025 mol.) of 1,3,5,7-tetramethylcyclotetrasiloxane (Gelest) is added along with a 20 μL portion of platinum-divinyltetramethyldisiloxane complex in xylene (Gelest), and the reaction mixture is heated to reflux for about 8 hours, after which an aliquot shows an NMR spectrum that indicates substantially all the allyl groups have reacted. The solvent is stripped off to yield the desired aminoethoxylate-substituted cyclotetrasiloxane, [Si(O)(CH$_3$)CH$_2$CH$_2$CH$_2$N{(OCH$_2$CH$_2$)$_5$OCH$_3$}$_2$]$_4$.

N-Allylethylenediamine

Intermediate Material R. A portion of about 120 g (about 2.0 mol.) of ethylenediamine is dissolved in about 300 ml of tetrahydrofuran in a 1000 ml round bottom flask equipped with magnetic stirring, reflux condenser and argon blanketing. A portion of about 76 g (about 1.0 mol.) of allyl chloride is added dropwise with good stirring over about one hour and then the system is brought to reflux for about 30 minutes. The reaction mixture is stripped to near dryness and about 300 ml of water and about 41 g (about 1.02 equivalents) sodium hydroxide is added with care to make the system strongly basic. The resulting solution is cooled to room temperature and extracted twice with about 200 ml portions of diethyl ether. The ether extracts are combined and dried over sodium sulfate and then fractionally distilled to yield a major fraction consisting of N-allylethylenediamine intermediate material suitable for use in hydrosilation reactions.

Hydrosilation of Allylethylenediamine by Cyclic Hydrosiloxanes

Intermediate Hydrosilation Material S. A portion of about 24 g (about 0.1 mol.) of 1,3,5,7-tetramethylcyclotetrasiloxane (Gelest) is dissolved in about 100 ml of dry toluene in a 250 ml, round bottom flask equipped with magnetic stirrer, reflux condenser and argon blanketing. A portion of about 40 g (about 0.40 mol.) of allylethylenediamine made as described above (Intermediate Material R) is added along with a portion of about 0.2 g (about 0.0005 mol.) of chloroplatinic acid (Aldrich), and the system is heated to reflux for about 4 hours. At this point, an aliquot examined by proton NMR shows that the resonances associated with the allyl group are substantially gone. The solvent is stripped off to yield the desired amino-functional cyclotetrasiloxane, [Si(O)(CH$_3$)(CH$_2$CH$_2$CH$_2$NHCH$_2$CH$_2$NH$_2$)]$_4$.

Vinyl-Terminated Oligosiloxanes with Pendant Amino Functionality

Intermediate Material T. In a 1000 ml, round bottom flask equipped with magnetic stirring, dropping funnel, thermometer, and a short fractionation column topped by a distillation head, is placed about 260.5 g (about 2.0 mol) vinyldimethylethoxysilane (Gelest) and about 191.3 g (about 1.0 mol) 3-aminopropylmethyldiethoxysilane. The reaction is stirred at room temperature as about 36 g (about 2 mol) water is added dropwise. The temperature is gradually increased until ethanol is being distilled from the reaction mixture and held at about 120° C. until no further ethanol is evolved. This gives the desired intermediate

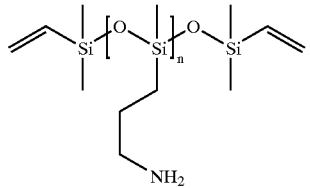

where the average value of n is about 1.

Preparation of Vinyl-Terminated Oligosiloxanes with Pendant Ethoxylate Functionality Intermediate Material U. In a 1000 ml, round bottom flask equipped with magnetic stirring, dropping funnel, thermometer, and a short fractionation column topped by a distillation head, is placed about 260.5 g (about 2.0 mol) vinyldimethylethoxysilane (Gelest) and about 426 g (about 1 mol) of the ethoxylate-substituted triethoxysilane prepared as above, CH$_3$(OCH$_2$CH$_2$)$_n$OCH$_2$CH$_2$CH$_2$Si(OCH$_2$CH$_3$)$_3$ with n of about 5. (Intermediate Material N). The reaction mixture is stirred at room temperature as about 36 g (about 2 mol) water is added dropwise. The temperature is gradually increased until ethanol is being distilled from the reaction mixture and is then held at about 120° C. until no further ethanol is evolved. This gives the desired intermediate

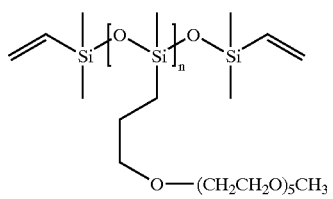

where the average value of n is about 1.

Polysiloxane Intermediates with Pendant Imidazole Groups

Intermediate Material V. Following generally the method of Fortuniak and Chojnowski, Polym. Bull. (Berlin) (1997), 38(4), 371–378, N-allylimidazole hydrochloride is hydrosilated methyldichlorosilane to a high yield of N-[3-(methyldichlorosilyl)propyl]imidazole hydrochloride which is hydrolyzed under controlled conditions to give a mixture of cyclic and linear polysiloxanes with pendant imidazole groups having the general structure

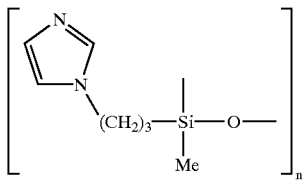

This mixture is used as intermediate V for incorporation of pendant imidazole groups into other polysiloxanes by re-equilibration.

Imidazole-Terminated Polydimethylsiloxane

Intermediate Material W. In a 250 ml, round bottom flask equipped with magnetic stirrer, reflux condenser, and argon blanketing are placed about 45 g (about 0.1 mol, Gelest) hydride-terminated polydimethylsiloxane with molecular weight of about 450 and about 17.5 g (about 0.23 mol, Aldrich) allyl chloride and about 0.6 g (about 0.0015 mol, Aldrich) chloroplatinic acid. The reaction mixture is heated to about 90° C. with stirring for about 18 hours. Excess allyl chloride is stripped out on a kugelrohr apparatus to give the chloropropyl terminated oligomer. Then, imidazole (about 68 g, about 1 mol, Aldrich) and 50 ml of dioxane are added and the reaction mixture is heated under reflux for 16 hours. Then, the reaction mixture is cooled to room temperature and sodium methoxide (about 10.8 g, about 0.20 moles as a 25% solution in methanol) is added. After stirring and allowing to stand for about 3 hours, the system is filtered and the filtrate is stripped of solvent and excess imidazole on a rotary evaporator and then on a kugelrohr at 150° C. for 2 hours at a vaccum of about 1 mmHg. to give the desired imidazole-terminated silicone with average n equal to about 5.

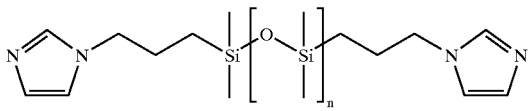

EXAMPLE I

Preparation of Curable Silicone with both Amine and Polyalkyleneoxy Functionality by Silanol Condensation In a 500 ml round bottom flask equipped with mechanical stirring, fractionation column and argon blanketing, are placed about 150 ml toluene, about 80 g silanol terminated polydimethylsiloxane (about 0.2 mol, Gelest, nominal molecular weight=400), about 42.6 g (about 0.1 mol.) of the $CH_3(OCH_2CH_2)_nOCH_2CH_2CH_2Si(CH_3)(OCH_2CH_3)_2$ with average n of about 5 prepared as above (Intermediate Hydrosilation Material N1), and about 22.1 g aminopropyltriethoxysilane (about 0.1 mol., Aldrich). The temperature is gradually raised to about 90° C. as ethanol distills out of the reaction mix. The heating and stirring is continued for about 6 hours after which the solvent is stripped from the reaction mixture to give the desired silicone having amine and ethoxylate functionality in addition to residual $SiOCH_2CH_3$, hydrolyzable groups.

Alternative Preparation The above synthesis is repeated without added solvent. The reaction temperature is raised to about 110° C. (instead of about 90° C.) for about 6 hours to give directly a curable silicone with amine and ethoxylate functionality.

Alternative Preparation The above synthesis without solvent is repeated, but with the addition of about 1 ml of a 10% solution of boron trifluoride in methanol to aid the condensation. In this case, the reaction temperature is raised only to about 90° C. for about 4 hours to give a curable silicone with amine and ethoxylate functionality.

EXAMPLE II

Quaternized Form of Curable Silicone with both Amine and Polyalkyleneoxy Functionality of Example I The synthesis is conducted similarly as in above Example I. The aminofunctional silicone obtained is mixed with about 140 ml of methanol and stirred vigorously at room temperature as about 12.6 g (about 0.1 mol.) of dimethyl sulfate is added dropwise. After about 10 minutes, about 21.6 g (about 0.1 mol.) of about 25% sodium methoxide in methanol (Aldrich) is added dropwise with stirring. An additional amount of about 12.6 g of dimethyl sulfate is added dropwise and after about 10 minutes, another about 21.6 g of about 25% sodium methoxide is added with continued vigorous stirring. Then a final amount of about 21.6 g of dimethyl sulfate is added and stirring is continued for about 30 minutes to give a nearly neutral reaction mixture. The precipitated salt is removed by filtration and the solvent is stripped under vacuum to give the desired curable silicone with quaternized amine, ethoxylate and alkoxysilane functionality.

EXAMPLE III

Preparation of Curable Silicone with both Amine and Polyethyleneoxy Functionality by Hydrosilation Example IIIa. With Methoxysilane Reactive Groups. An amount of about 10.2 g (about 0.02 mol.) of $CH_3(OCH_2CH_2)_nOCH_2CH=CH_2$ with average n of about 10, prepared as above (Intermediate Material J1) is dissolved in about 150 ml toluene in a 500 ml round bottom flask equipped with magnetic stirring, short path distillation head and argon blanketing. About 50 ml of toluene is distilled off to dry the system and the resulting solution is cooled to room temperature. The distillation head is replaced by a reflux condenser. Then, a portion of about 62 g of a methyl terminated copolymer of methylhydrosiloxane and dimethylsiloxane with MW of about 62,000 and about 6 mole% hydrosiloxane groups (about 0.001 mole, about 0.05 equivalents SiH, Gelest) is added along with about a 20 µL portion of platinum-divinyltetramethyldisiloxane complex in xylene (Gelest). The system is heated under reflux for about 2 hours after which a stripped aliquot shows no residual allyl resonance in the proton NMR spectrum in $CDCl_3$. Then, N-allylethylenediamine (about 2.0 g, about 0.02 mol.) prepared as above (Intermediate Material R) is added to the bulk reaction mixture and heating at reflux is continued for about 2 hours, at which time an aliquot shows no remaining allyl resonances by NMR. Then, about 1.32 g (about 0.01 mol.) vinylmethyldimethoxysilane (Gelest) is added and the reaction mixture is heated at about 100° C. for about 8 hours. The solvent is then stripped off to give the desired curable silicone with amino, methyl-capped ethoxylate, and $SiOCH_3$ functionality.

Example IIIb. Silicones with Ethoxylated-proproxylated Groups. The above preparation is repeated except that the ethoxylated intermediate J1 is replaced by an equimolar amount of the propoxylated-ethoxylated analog, intermediate J3. This produces the desired curable silicone with amino, methyl-capped alkoxylate, and $SiOCH_3$ functionality.

Example IIIc. Silicones with Hindered Alcohol Capping Groups. The preparation is repeated except that the ethoxylated intermediate J1 is replaced by an equimolar amount of the analog capped with a hindered alcohol, J4. This produces the desired curable silicone with amino and $SiOCH_3$ functionality, and —$CH_2C(CH_3)_2(OH)$— capped ethoxylate pendant groups.

Example IIId. Silicones with Tetrahydropyranyl Capping Groups. The preparation is repeated except that the ethoxylated intermediate J1 is replaced by an equimolar amount of the analog having a tetrahydropyranyl (THP) capping group, Intermediate Material K2. In this case, a few drops of triethylamine is added along with the THP derivative to ensure that the system remains on the alkaline side. This gives the desired curable silicone with amino, THP-capped ethoxylate, and $SiOCH_3$ functionality. This material is further transformed by mixing with methanol and adding enough methanesulfonic acid to make the system very slightly acidic to release the THP groups and give a solution containing the desired curable silicone with amino, uncapped ethoxylate, and $SiOCH_3$ functionality.

EXAMPLE IV

Preparation of Curable Silicone with both Amine and Polyethyleneoxy Functionality by Hydrosilation, and with Non-terminal, Reactive Si—$OCH_3$ Groups on the Silicone Backbone The synthesis of Example III is repeated, except that instead of adding the vinylmethyldimethoxysilane, about 2 g (about 0.06 mol) methanol containing about 12% $BF_3$ (Aldrich) is added and the system is heated at about 60° C. for about 12 hours as hydrogen is evolved. The solvent is then stripped off under vacuum to obtain the desired curable silicone with amino, methyl-capped ethoxylate, and non-terminal, reactive $SiOCH_3$ functionality on the silicone backbone.

EXAMPLE V

Preparation of Curable Silicone with both Amine and Polyethyleneoxy Functionality by Hydrosilation, With Acetoxysilane Functionality for Increased Moisture Sensitivity An amount of about 10.2 g (about 0.02 mol.) of $CH_3(OCH_2CH_2)_nOCH_2CH$=$CH_2$ with average n of about 10, prepared as above (Intermediate Material J1), is dissolved in about 150 ml toluene in a 500 ml round bottom flask equipped with magnetic stirring, short path distillation head and argon blanketing. About 50 ml of toluene is distilled off to dry the system and the resulting solution is cooled to room temperature. The distillation head is replaced by a reflux condenser. Then, an amount of about 62 g of a methyl terminated copolymer of methylhydrosiloxane and dimethylsiloxane with MW of about 62,000 and about 6 mole % hydrosiloxane groups (about 0.001 mole, about 0.05 equivalents SiH, Gelest) is added along with about 1.9 g (about 0.0046 mol) hexachloroplatinic acid. The system is heated under reflux for about 2 hours after which a stripped aliquot shows no residual allyl resonance in the proton NMR spectrum in $CDCl_3$. Then, dimethylallylamine (about 1.7 g, about 0.02 mol., Across Organics) is added to the bulk reaction mixture and heating is resumed for about 12 hours at about 60° C., at which time an aliquot shows no remaining allyl resonances by NMR. Then, about 1.9 g (about 0.01 mol.) vinylmethyldiacetoxysilane (Gelest) is added and the reaction mixture is heated at about 100° C. for about 8 hours. The solvent is then stripped off to give the desired curable silicone with amino, ethoxylate, and SiOAc functionality.

EXAMPLE VI

Preparation of Curable Silicone with both Amine and Polyethyleneoxy Functionality by Equilibration of Polysiloxanes Example VIa. Silicone with Methyl-Capped Polyethyleneoxy Functionality. A 500 ml round bottom flask is set up with magnetic stirring, argon blanketing, and distillation head. In the flask are placed about 150 ml toluene, about 25.6 g (about 0.04 mol) of the amine-substituted cyclotetrasiloxane, $[Si(O)(CH_3)(CH_2CH_2CH_2NHCH_2CH_2NH_2)]_4$, prepared as above (Intermediate Hydrosilation Material S), about 85.1 g (about 0.04 mol.) of the ethoxylate-substituted cyclotetrasiloxane, $[Si(O)(CH_3)CH_2CH_2CH_2(OCH_2CH_2)_{10}OCH_3]_4$, prepared as above, (Intermediate Hydrosilation Material O) and about 100.8 g (about 0.34 mol.) of octamethylcyclotetrasiloxane (Gelest). The system is taken to the boiling point and about about 50 ml of toluene is distilled out to dry the system. Then, about 9 g (about 0.01 mol.) of methoxy terminated polydimethylsiloxane with molecular weight of about 900 (Gelest) is added along with about 0.5 g of tetramethylammonium siloxanolate (Gelest) as a catalyst and the distillation head is replaced with a reflux condenser. Then the reaction mixture is heated to about 95° C. and held there for about 18 hours. Acetic acid about 0.2 g (about 0.03 mol.) is added sufficient to neutralize the strong base and the solvent is stripped on a rotary evaporator to yield the desired curable silicone with amine, ethoxylate, and $SiOCH_3$ functionality.

Example VIb. Silicone with Tetrahydropyranyl-Capped Polyethyleneoxy Functionality. The synthesis is repeated except that the $[Si(O)(CH_3)CH_2CH_2CH_2(OCH_2CH_2)_{10}OCH_3]_4$ is replaced by an equimolar amount of the THP-capped ethoxylate-substituted cyclotetrasiloxane, $[Si(O)(CH_3)CH_2CH_2CH_2(OCH_2CH_2)_{10}O\text{-}THP]_4$, prepared as above (Intermediate Hydrosilation Material P). In this case, acetic acid is not added after the equilibration and the desired curable silicone with amine, ethoxylate, and $SiOCH_3$ functionality also having THP-capped ethoxylate chains is obtained.

Example VIc. Silicone with Hydroxyl-Capped Polyethyleneoxy Functionality. A portion of the silicone with tetrahydropyranyl-capped polyethyleneoxy functionality material prepared as above is taken up in methanol containing enough acetic acid to neutralize the base and provide mild acidity to release the THP protecting group. The resulting reaction mixture is partially stripped under vacuum to remove part of the methanol and yield a solution of the desired curable silicone with amine, hydroxyl-terminated ethoxylate, and $SiOCH_3$ functionality.

Example VId. Silicone with Hydroxyl-Capped Polyethyleneoxy Functionality. The synthesis is repeated again, except that the more highly ethoxylated THP-capped ethoxylate-substituted cyclotetrasiloxane $[Si(O)(CH_3)CH_2CH_2CH_2(OCH_2CH_2)_{24}O\text{-}THP]_4$ (P1) is used to prepare the desired THP-capped curable silicone.

Example VIe. A portion of the silicone of Example VId is hydrolyzed as described above, to give the corresponding hydroxyl-terminated silicone.

EXAMPLE VII

Preparation of Curable Silicone with both Amine and Polyethyleneoxy Functionality by Hydrosilation of Capped, Ethoxylated Allylamine Example VIIa. Silicone with SiOCH Functionality and Methyl-Capped Polyethyleneoxy Functionality. An amount of about 21 g (about 0.04 mol.) of capped, ethoxylated allylamine, $CH_2$=$CHCH_2N[(CH_2CH_2O)_nCH_3]_2$ with average n of about 5, prepared as above (Intermediate Material G), is dissolved in about 150 ml toluene in a 500 ml round bottom flask equipped with magnetic stirring, short path distillation head and argon blanketing. About 50 ml of toluene is distilled off to dry the system and the resulting solution is cooled to room temperature. The distillation head is replaced by a reflux condenser. Then, a portion of about 62 g of a methyl terminated copolymer of methylhydrosiloxane and dimethylsiloxane with MW of about 62,000 and about 6 mole % hydrosiloxane groups (about 0.001 mole, about 0.05 equivalents SiH, Gelest) is added along with about a 20 μL portion of platinum-divinyltetramethyldisiloxane complex in xylene (2.4% Pt, Gelest). The system is heated under reflux for about 4 hours after which a stripped aliquot shows no residual allyl resonance in the proton NMR spectrum in $CDCl_3$ Then, about 1.3 g (about 0.01 mol.) vinylmethyldimethoxysilane (Gelest) is added and the reaction mixture is heated at about 100° C. for about 8 hours. The solvent is then stripped off to give the desired curable silicone with ethoxylated amino, and $SiOCH_3$ functionality.

Example VIIb. The preparation is repeated, except that the more highly ethoxylated allylamine homolog, $CH_2$=$CHCH_2N[(CH_2CH_2O)_nCH_3]_2$ with average n of about 22 (Intermediate Material G2) is used to give the desired curable silicone having ethoxylated amino and $SiOCH_3$ functionality.

Example VIIc. Silicone with $SiOCOCH_3$ Functionality. The preparation of Example VIIb is repeated, except that the vinylmethyldimethoxysilane is replaced by an equimolar amount of vinylmethyldiacetoxysilane. This yields the desired curable silicone with ethoxylated amine and SiOAc functionality.

Example VIId. Silicone with $SiOCH_3$ Functionality and Hindered Hydroxyisobutylyl-Capped Polyethyleneoxy Functionality. The first preparation in this group, Example VIIa, is repeated except that the methyl capped, ethoxylated allylamine derivative is replaced by about 43.2 g (about 0.04 mol.) of the hindered hydroxyisobutyl-capped analog, $CH_2$=$CHCH_2N[(CH_2CH_2O)_n$—$CH_2C(OH)(CH_3)_2]_2$ with average n of about 10 prepared as described above (Intermediate Material H). This yields the desired curable silicone with ethoxylated amino and $SiOCH_3$ functionality and hindered alcohol-capped ethoxylate groups.

EXAMPLE VIII

Preparation of Curable Silicone with Ethoxylated Amino Functionality by Equilibration of Polysiloxanes A 500 ml round bottom flask is set up with mechanical stirring, argon blanketing, and short path distillation head. In the flask are placed about 200 ml toluene, about 93.6 g (about 0.04 mol) of the aminoethoxylate-substituted cyclotetrasiloxane, $[Si(O)(CH_3)CH_2CH_2CH_2N\{(OCH_2CH_2)_5OCH_3\}_2]_4$ prepared as above (Intermediate Hydrosilation Material Q), and about 100.8 g (about 0.34 mol.) octamethylcyclotetrasiloxane (Gelest). The system is taken to the boiling point and about 50 ml of toluene is distilled out to dry the system. Then, about 9 g (about 0.01 mol.) of methoxy terminated polydimethylsiloxane with molecular weight of about 900 (Gelest) is added along with about 0.5 g of tetramethylammonium siloxanolate (Gelest) and the distillation head is replaced with a reflux condenser. Then the reaction mixture is heated to about 95° C. and held there for about 18 hours. Acetic acid, about 0.2 g (about 0.03 mol.), is added sufficient to neutralize the strong base and the solvent is stripped on a rotary evaporator to yield the desired curable silicone with ethoxylated amino, and $SiOCH_3$ functionality.

Quaternized Form. The synthesis is repeated, but rather than adding acetic acid near the end, the reaction mixture is cooled to room temperature and about 5.04 g dimethyl sulfate (about 0.16 mol. Aldrich) is added dropwise with good stirring. Stirring is continued at room temperature for about 3 hours. Then the solvent is stripped under vacuum to give the desired curable silicone with quaternized, ethoxylated amino groups and $SiOCH_3$ functionality.

EXAMPLE IX

Preparation of Curable Silicone with Ethoxylate and Amino Functionality from Vinyl-Terminated and Silane-Terminated Units In a 2000 ml, round bottom flask equipped with mechanical stirring, reflux condenser, and argon blanketing, are placed about 200 ml toluene, about 405 g (about 0.90 mol) hydride-terminated polydimethylsiloxane (Gelest), about 137.5 g (0.50 mol) of the vinyl-terminated oligosiloxane with pendant amino groups,

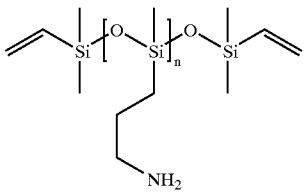

where average n is about 1, prepared as described above (Intermediate Material T), and about 255 g (about 0.50 mol) of the vinyl-terminated oligosiloxane with pendant ethoxylate groups,

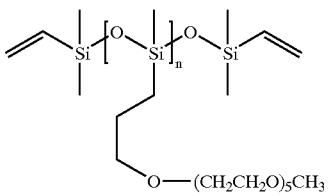

where average n is about 1, prepared as described above (Intermediate Material U). The system is stirred at about 80° C. and about 4.1 g (about 0.01 mol) chloroplatinic acid is added in small portions to avoid an excessive exotherm. After about 6 hours, the temperature was raised to about 100° C. and held there for another about 18 hours. Then the reaction mixture is cooled to about 80° C. and about 33.7 g (about 0.3 mol) trimethoxysilane (Gelest) is added and the system is heated at about 80° C. for about 6 hours and then the internal temperature is raised to about 95° C. and held there for about 18 hours. An aliquot examined by proton NMR indicates that the vinyl functionality has disappeared. The solvent and excess trimethoxysilane are stripped on a rotary evaporator to yield the desired curable silicone with amino, ethoxylate, and terminal, reactive trimethoxysilane functionality.

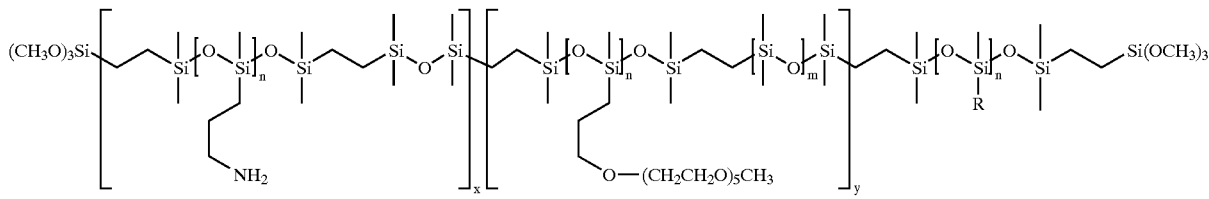

EXAMPLE X

Preparation of Curable Silicone with both Imidazole (or Imidazolium) and Polyethyleneoxy Functionality by Silanol Condensation Example Xa. Imidazole Form. In a 500 ml round bottom flask equipped with mechanical stirring, fractionation column and argon blanketing, are placed about 150 ml toluene, about 80 g silanol terminated polydimethylsiloxane (about 0.2 mol, Gelest, molecular weight of about 400), about 42.6 g (0.1 mol.) of the $CH_3(OCH_2CH_2)_nOCH_2CH_2CH_2Si(CH_3)(OCH_2CH_3)_2$ with average n of about 5 prepared as above (Intermediate Material N1), and about 23 g N-trimethoxysilylpropylimidazole (about 0.1 mol., Pfaltz & Bauer Inc., Waterbury, Conn.). The temperature is gradually raised to about 90° C. as ethanol distills out of the reaction mix. The heating and stirring is continued for about 6 hours after which the solvent is stripped from the reaction mixture to give the desired curable silicone having imidazole and polyethoxylate functionality in addition to residual $SiOCH_3$, hydrolyzable groups.

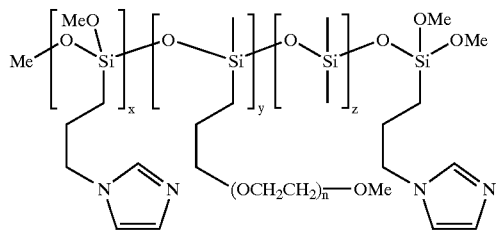

Example Xb. Imidazolium Form. A portion of the imidazole-substituted silicone prepared above is dissolved in methylene chloride and stirred vigorously at room temperature while sufficient dimethyl sulfate to quaternize the imidazole functions is added dropwise. After stirring for about 1 hour, a few drops of imidazole are added to consume any excess alkylating agent and buffer any traces of acid. The solvent is then stripped off on the rotary evaporator to give the desired curable silicone with imidazolium groups, polyethoxylate groups and residual hydrolyzable $SiOCH_3$ groups.

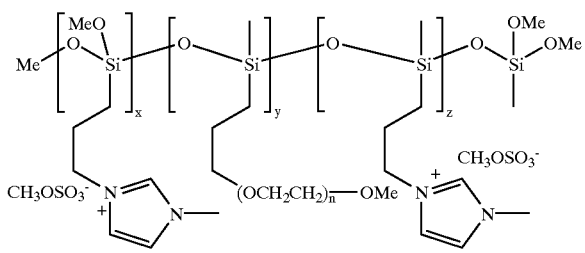

EXAMPLE XI

Preparation of Curable Silicone with both Imidazole and Polyetheneoxy Functionality by Hydrosilation With Methoxysilane Reactive Groups. A portion of about 10.2 g (about 0.02 mol.) of $CH_3(OCH_2CH_2)_nOCH_2CH=CH_2$ with average n of about 10, prepared as above (Intermediate Material J1), is dissolved in about 150 ml toluene in a 500 ml round bottom flask equipped with magnetic stirring, short path distillation head and argon blanketing. About 50 ml of toluene is distilled off to dry the system and the resulting solution is cooled to room temperature. The distillation head is replaced by a reflux condenser. Then, a portion of about 62 g of a methyl terminated copolymer of methylhydrosiloxane and dimethylsiloxane with MW of about 62,000 and about 6 mole % hydrosiloxane groups (about 0.001 mole, about 0.05 equivalents SiH, Gelest) is added along with an amount of about 40 μL of platinum-divinyltetramethyldisiloxane complex in xylene (Gelest). The system is heated under reflux for about 2 hours, after which a stripped aliquot shows no residual allyl resonance in the proton NMR spectrum in $CDCl_3$. Then, allyl chloride (about 1.53 g. about 0.02 mol., Aldrich) is added to the bulk reaction mixture and heating at reflux is continued for about 2 hours, at which time an aliquot shows no remaining allyl resonances by NMR, but some SiH groups remain as indicated by infrared spectroscopy. Then, about 1.48 g (about 0.01 mol.) vinyltrimethoxysilane (Gelest) is added and the reaction mixture is heated at about 100° C. for about 8 hours. NMR spectroscopy indicates that all vinyl groups have disappeared and infrared spectroscopy indicates that only traces of SiH functionality remain. Then, imidazole (about 5 g, about 0.074 mol, Aldrich) is added and the reaction mixture is heated at reflux for about 16 hours. The reaction mixture is cooled to room temperature and sodium methoxide (about 1 g, about 0.19 mol in 25% solution in methanol, Aldrich) is added, and after stirring and allowing to stand for about 3 hours, the reaction mixture is filtered. The solvent is then stripped from the filtrate, first on a rotary evaporator and then on a kugelrohr at 140° C. for about 1 hour to give the desired curable silicone with imidazole, polyethoxylate, and $SiOCH_3$ functionality.

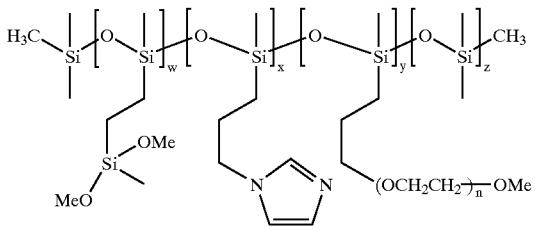

EXAMPLE XII

Preparation of Curable Silicone with both Imidazole and Polyetheneoxy Functionality by Hydrosilation, with Non-terminal Si—OCH$_3$ Functionality on the Silicone Backbone The synthesis of Example XI is repeated, except that the vinyltrimethoxysilane is not added and after the stripping of solvent and excess imidazole, the hydrosilane-containing polymer is again taken up in about 150 ml of toluene and treated with about 2 g (0.06 mol) methanol containing about 12% BF$_3$ (Aldrich) and the system is heated at about 60° C. for about 12 hours as hydrogen is evolved. The solvent is then stripped off under vacuum to obtain the desired curable silicone with imidazole, ethoxylate, and non-terminal, reactive SiOCH$_3$ functionality on the silicone backbone.

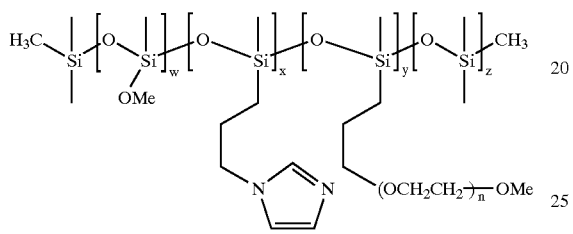

EXAMPLE XIII

Preparation of Curable Silicone with both Imidazole and Polyetheneoxy Functionality by Hydrosilation, with Acetoxysilane Functionality for Increased Moisture Sensitivity A portion of about 10.2 g (about 0.02 mol.) of CH$_3$(OCH$_2$CH$_2$)$_n$OCH$_2$CH=CH$_2$ with average n of about 10, prepared as above (Intermediate Material J1), is dissolved in about 150 ml toluene in a 500 ml round bottom flask equipped with magnetic stirring, short path distillation head and argon blanketing. About 50 ml of toluene is distilled off to dry the system and the resulting solution is cooled to room temperature. The distillation head is replaced by a reflux condenser. Then, a portion of about 62 g of a methyl terminated copolymer of methylhydrosiloxane and dimethylsiloxane with Mw of about 62,000 and about 6 mole % hydrosiloxane groups (about 0.001 mole, about 0.05 equivalents SiH, Gelest) is added along with a portion of about 40 μL of platinum-divinyltetramethyldisiloxane complex in xylene (Gelest). The system is heated under reflux for about 2 hours after which a stripped aliquot shows no residual allyl resonance in the proton NMR spectrum in CDCl$_3$. Then, allyl chloride (about 1.53 g., about 0.02 mol, Aldrich) is added to the bulk reaction mixture and heating is resumed for about 12 hours at about 60° C., at which time an aliquot shows only traces of remaining allyl resonances by NMR. Then, imidazole (about 5 g, about 0.074 mol, Aldrich) is added and the reaction mixture is heated at reflux for about 16 hours to displace the chloro groups with imidazole groups. The reaction mixture is cooled to room temperature and sodium methoxide (about 1 g, about 0.019 mol in 25% solution in methanol, Aldrich) is added, and after stirring and allowing to stand for about 3 hours, the reaction mixture is filtered. The solvent is then stripped off of the filtrate, first on a rotary evaporator, and then on a kugelrohr at 140° C. for about 1 hour to give an intermediate still containing some hydrosilane functionality. The material is taken up again in about 150 ml of toluene and a fresh portion of about 40 μL of platinum-divinyltetramethyldisiloxane complex in xylene is added. Then, about 1.9 g (about 0.01 mol.) vinylmethyldiacetoxysilane (Gelest) is added and the reaction mixture is heated at about 100° C. for about 8 hours. The solvent is then stripped off to give the desired curable silicone with imidazole, polyethoxylate, and SiOAc functionality.

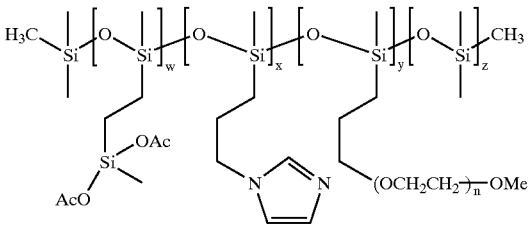

Hydrophilic Non-Curable Silicones

Some novel hydrophilic non-curable silicones are also useful for the purpose of the present invention. Following are nonlimiting examples of hydrophilic non-curable silicones of the present invention.

EXAMPLE XIV

Preparation of Non-Curable Silicone with both Amine and Polyethyleneoxy Functionality by Equilibration of Polysiloxanes A 500 ml round bottom flask is set up with magnetic stirring, argon blanketing, and distillation head. In the flask are placed about 200 ml toluene, about 25.6 g (about 0.04 mol) of the amine-substituted cyclotetrasiloxane, [Si(O)(CH$_3$)(CH$_2$CH$_2$CH$_2$NHCH$_2$CH$_2$NH$_2$)]$_4$, prepared as above (Intermediate Hydrosilation Material S), about 85.1 g (about 0.04 mol.) of the ethoxylate-substituted cyclotetrasiloxane, [Si(O)(CH$_3$)CH$_2$CH$_2$CH$_2$(OCH$_2$CH$_2$)$_{10}$OCH$_3$]$_4$, prepared as abov (Intermediate Hydrosilation Material O), about 100.8 g (about 0.34 mol.) octamethylcyclotetrasiloxane (Gelest) and about 2.5 g (about 0.01 mol.) 1,3-bis(3-aminopropyl)tetramethyldisiloxane (Gelest). The system is taken to the boiling point and about 50 ml of toluene is distilled out to dry the system. Then, about 1 g of tetramethylammonium siloxanolate (Gelest) is added and the distillation head is replaced with a reflux condenser. The reaction mixture is heated to about 95° C. and held there for about 18 hours. Acetic acid about 0.2 g (about 0.03 mol.) is added sufficient to neutralize the strong base and the solvent is stripped on a rotary evaporator to yield the desired silicone with amino and ethoxylate functionality.

EXAMPLE XV

Preparation of Silicone with both Imidazole and Polyol Functionality by Hydrosilation Silicone with Imidazolylpropyl Pendant Groups. A portion of about 10.2 g (about 0.02 mol.) of CH$_3$(OCH$_2$CH$_2$)$_n$OCH$_2$CH=CH$_2$ with average n of about 10, prepared as above (Intermediate Material J1), is dissolved in about 150 ml toluene in a 500 ml round bottom flask equipped with magnetic stirring, short path distillation head and argon blanketing. About 50 ml of toluene is distilled off to dry the system and the resulting solution is cooled to room temperature. The distillation head is replaced by a reflux condenser. Then, a portion of about 62 g of a methyl terminated copolymer of methylhydrosiloxane and dimethylsiloxane with MW of about 62,000 and about 6 mole % hydrosiloxane groups (about 0.001 mole, about 0.05 equivalents SiH, Gelest) is added along with an amount of about 50 μL of platinum-divinyltetramethyldisiloxane complex in xylene (Gelest). The system is heated under reflux for about 2 hours after which a stripped aliquot shows no residual allyl resonance in the proton NMR spectrum in $CDCl_3$. Then, allyl chloride (about 2.28, about 0.03 mol., Aldrich) is added to the bulk reaction mixture and heating at reflux is continued for about 5 hours, at which time an aliquot shows no remaining SiH bonds by Infrared spectroscopy. Then, imidazole (about 6.8 g, about 0.10 mol, Aldrich) is added and the reaction mixture is heated at reflux for about 16 hours. The reaction mixture is cooled to room temperature and sodium methoxide (about 1.62 g, about 0.03 mol in 25% solution in methanol, Aldrich) is added and after stirring, and allowing to stand for about 3 hours, the reaction mixture is filtered. The solvent is then stripped off of the filtrate, first on a rotary evaporator, and then on a kugelrohr at 140° C. for about 1 hour to give the desired silicone with both polyethoxylate and imidazole functionality.

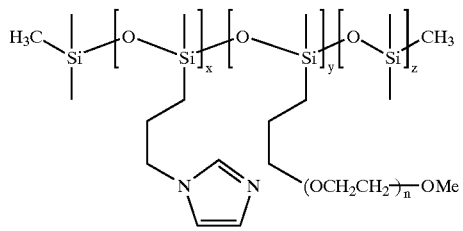

EXAMPLE XVI

Preparation of Silicone with both Imidazole and Polyol Functionality by Equilibration Polysiloxanes A 500 ml round bottom flask is set up with magnetic stirring, argon blanketing, and distillation head. In the flask are placed about 150 ml toluene, about 8.4 g (about 0.05 equiv.) of the imidazole-substituted oligosiloxanes, [Si(O)(CH3)(CH2CH2CH2-Imidazole)]$_n$, prepared as above (Intermediate Material V), about 57.6 g (about 0.10 equiv.) of the ethoxylate-substituted cyclotetrasiloxane, [Si(O)(CH$_3$) CH$_2$CH$_2$CH$_2$(OCH$_2$CH$_2$)$_{10}$OCH$_3$]$_4$, prepared as above (Intermediate Material O), and about 100.8 g (about 1.36 equiv.) octamethylcyclotetrasiloxane (Gelest). The system is taken to the boiling point and about 50 ml of toluene is distilled out to dry the system. Then, about 1 g of tetramethylammonium siloxanolate (Gelest) is added and the distillation head is replaced with a reflux condenser. The reaction mixture is heated to about 95° C. and held there for about 18 hours. Acetic acid, about 0.2 g (about 0.03 mol.) is added, sufficient to neutralize the strong base and the solvent is stripped on a rotary evaporator to yield the desired silicone with imidazole and polyethoxylate functionality.

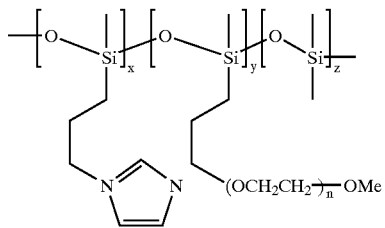

EXAMPLE XVII

Preparation of Silicone with Imidazole-Terminated Ethoxylate Pendant Groups by Hydrosilation A portion of about 33.6 g (0.06 mol.) of imidazole-terminated allyl ethoxylate, $CH_2$=$CHCH_2(OCH_2CH_2)_n$-imidazole, with average n of about 10, prepared as above (Intermediate Material M), is dissolved in about 150 ml toluene in a 500 ml round bottom flask equipped with magnetic stirring, short path distillation head and argon blanketing. About 50 ml of toluene is distilled off to dry the system and the resulting solution is cooled to room temperature. The distillation head is replaced by a reflux condenser. Then, an amount of about 62 g of a methyl terminated copolymer of methylhydrosiloxane and dimethylsiloxane with MW of about 62,000 and about 6 mole % hydrosiloxane groups (about 0.001 mole, about 0.05 equivalents SiH, Gelest) is added along with a portion of about 20 μL of platinum-divinyltetramethyldisiloxane complex in xylene (Gelest). The reaction mixture is then heated at reflux for about 18 hours. At this point, infrared spectroscopy indicates that essentially all the SiH functionality has been consumed. The solvent is removed by stripping on a rotary evaporator to give the desired silicone with imidazole-capped ethoxylate groups along with a small residual amount of unreacted starting imidazole-capped allyl ethoxylate.

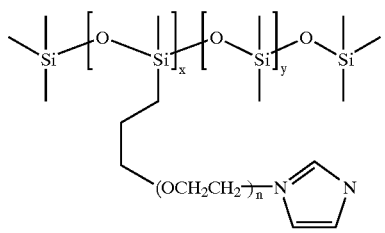

EXAMPLE XVIII

Preparation of Ethoxylated Silicone with Silicone Blocks, Polyethoxylate Blocks, and Imidazolium Groups in the Main Chain An amount of about 66.6 g (about 0.1 mol) of imidazole-terminated silicone (Intermediate Material W) is placed in a 500 ml, round bottom flask with about 47.3 g (about 0.09 mol, Aldrich) of polyethylene glycol, diglycidyl ether of molecular weight 526 and about 10.8 g (about 0.18 mol) acetic acid. The reaction mixture is stirred vigorously with a mechanical stirrer and is heated to about 90° C. and held there about 18 hours. This produces the desired silicone containing both polyethoxylate and imidazolium groups in the chain.

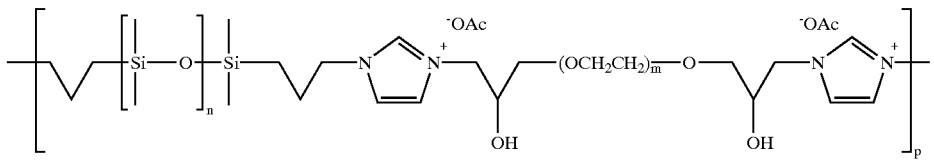

where n is about 5 and m is about 9.

Although many of the syntheses illustrated hereinabove tend to give random polymers, the skilled practitioner can select appropriate variations on them to give some degree of blockiness. For example, EP 786488 published Jul. 30, 1997 illustrates making blocky polymers of dimethylsiloxane and hydromethylsiloxane and is incorporated herein by reference. If these blocky materials are used in the syntheses in which pendant groups are attached by hydrosilation methods, blocky analogs of some of the illustrated materials are obtained. The polymer of Example IX which is assembled by hydrosilation to form the backbone and having terminal reactive silane groups is a block copolymer.

The following are non-limiting examples of compositions of the present invention.

The following fabric care compositions of Examples 1 and 2 are prepared by mixing and dissolving the ingredients into clear or translucent solutions.

EXAMPLE 1

| Ingredients | 1a Wt. % | 1b Wt. % | 1c Wt. % | 1d Wt. % | 1e Wt. % |
|---|---|---|---|---|---|
| Silicone of Example IIIb | 1.5 | — | — | — | — |
| Silicone of Example V | — | 1 | — | — | — |
| Silicone of Example VId | — | — | 1.5 | — | — |
| Silicone of Example VIIb | — | — | — | 1 | — |
| Silicone of Example VIId | — | — | — | — | 2 |
| Perfume | 0.06 | 0.1 | 0.05 | 0.05 | 0.06 |
| Sorbitan monolaurate | 0.5 | — | 0.5 | 0— | 2 |
| Hexadecyltrimethyl ammonium chloride | — | — | 0.1 | — | 0.2 |
| Kathon CG | 3 ppm | 3 ppm | 3 ppm | 3 ppm | 3 ppm |
| Deionized Water | Bal. | Bal. | Bal. | Bal. | Bal. |

Aqueous compositions of Examples 1 are used to treat fabric via, e.g., spraying, soaking, or dipping to obtain one or more of the following fabric care benefits: fabric wear reduction, fabric wear resistance, color maintenance, color restoration, fabric pilling reduction, fabric color maintenance, fabric soiling reduction, fabric soil release, fabric comfort, wrinkle resistance, wrinkle reduction, anti-shrinkage, and/or fabric shape retention.

EXAMPLE 2

| Ingredients | 2a Wt. % | 2b Wt. % | 2c Wt. % | 2d Wt. % | 2e Wt. % |
|---|---|---|---|---|---|
| Silicone of Example IIIa | 25 | — | — | — | — |
| Silicone of Example VIe | — | 25 | — | — | — |
| Silicone of Example XIIb | — | — | 20 | — | — |
| Silicone of Example Xb | — | — | — | 10 | — |
| Silicone of Example XIIa | — | — | — | — | 40 |
| Perfume | 1 | 1.2 | 0.8 | — | 1.5 |
| Ethyl Alcohol | 74 | 73.8 | — | 75 | 50 |
| Isopropyl Alcohol | 0.5 | — | 79.8 | 15 | 8.5 |

Alcoholic concentrated compositions of Examples 2 are diluted with water to obtain usage compositions for treating fabric via, e.g., spraying, soaking, dipping to obtain one or more of the following fabric care benefits: fabric wear reduction, fabric wear resistance, color maintenance, color restoration, fabric pilling reduction, fabric color maintenance, fabric soiling reduction, fabric soil release, fabric comfort, wrinkle resistance, wrinkle reduction, anti-shrinkage, and/or fabric shape retention.

Non-limiting examples of car care compositions:

EXAMPLE 3

| Ingredients | 3a Wt. % | 3b Wt. % | 3c Wt. % | 3d Wt. % | 3e Wt. % |
|---|---|---|---|---|---|
| Silicone of Example IIIa | 6 | — | — | — | — |
| Silicone of Example VIa | — | 6 | — | — | — |
| Silicone of Example VIIb | — | — | 6 | — | — |
| Silicone of Example XI | — | — | — | 6 | — |
| Silicone of Example XIII | — | — | — | — | 6 |
| Dimethylsiloxane 350 Cts | 6 | 6 | −6 | 6 | 6 |
| Acid Type Wax | 2 | 2 | 4 | 4 | 4 |
| Oleic acid | 3.2 | 3.2 | 3.2 | 3.2 | 3.2 |
| Morpholine | 1.1 | 1.1 | 1.1 | 1.1 | 1.1 |
| Triethanolamine (2% solution) | 5 | 5 | 15 | 15 | 15 |
| Carbopol 934 Stabilizer (2% solution)[a] | 5 | 5 | 15 | 15 | 15 |
| Isopar L Solvent[b] | 4.3 | 4.3 | 4.3 | 4.3 | 4.3 |
| Diatomaceous Silica[c] | 11 | 11 | 11 | 11 | 11 |
| Mineral Spirits (odorless) | 10 | 10 | 10 | 10 | 10 |
| Water | Bal. | Bal. | Bal. | Bal. | Bal. |

[a]Carbopol 934 Stabilizer, carboxypolymethylene polymer with a molecular weight of about 1,000,000 from B. F. Goodrich Chemical Company.
[b]Isopar L Solvent isoparaffinic hydrocarbon with a mid boiling point of about 195° C., from Exxon Company.
[c]Processed diatomaceous silica with about 0.1% retained on 325 mesh.

Non-limiting examples of personal care compositions:
Hair spray compositions:

EXAMPLE 4

| Ingredients | 4a Wt. % | 4b Wt. % | 4c Wt. % |
| --- | --- | --- | --- |
| Silicone of Example Xb | 2.2 | — | — |
| Silicone of Example XVI | — | 2.2 | — |
| Silicone of Example XVIII | — | — | 2.2 |
| Dimethylsiloxane 350 Cts | 0.2 | 0.2 | 0.2 |
| Perfume | 0.1 | 0.1 | 0.1 |
| Water | — | 22.5 | 22.5 |
| Ethyl Alcohol | 97.5 | 75 | 75 |
| | 100 | 100 | 100 |

What is claimed is:

1. A silicone polymer which conforms to the following structure:

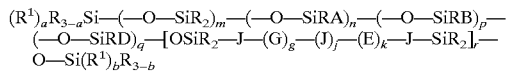
$(-O-SiRD)_q-[OSiR_2-J-(G)_g-(J)_j-(E)_k-J-SiR_2]_r-$
$O-Si(R^1)_bR_{3-b}$ wherein:
each R is the same or different and is selected from the group consisting of alkyl, aryl, and mixtures thereof;
each A is the same or different and is selected from the group consisting of hydrogen, —OH, —OR, —OCOCH$_3$, —CH$_2$CH$_2$Si(OR)$_3$, —CH$_2$CH$_2$Si(OR)$_2$R, —CH$_2$CH$_2$Si(OR)R$_2$, and mixtures thereof;
each optional B is an —X—E group with each X being a hydrocarbon or oxygenated hydrocaxbon linking group, and each E being a cationic nitrogen functional group;
each optional D is a poly(ethyleneoxy/propyleneoxy) group having the structure:

wherein each Z is a linking group, selected from the group consisting of hydrocarbon linking group, oxygenated hydrocarbon linking group, aminohydrocarbon linking group, and mixtures thereof; each R$^3$ is the same or different and is selected from the group consisting of hydrogen, R, E, JE, —CH$_2$CH(R)OH, —CH$_2$C(R)$_2$OH, —CH$_2$CH(OH) CH$_2$OR, —CH$_2$CH(OH)CH$_2$(OCH$_2$CH$_2$)$_e$OR, tetrahydropyranyl, —CH(R)OR, C(O)H, —C(O)R, and mixtures thereof; each c is at least about 2, total c (for all polyalkyleneoxy pendant groups) has a value of from about 4 to about 2500; total d has a value of from 0 to about 1000, c is equal or larger than d; and each e is from 1 to about 20;
each optional G is —O(C$_2$H$_4$O)$_v$(C$_3$H$_6$O)$_w$—; each J is selected from the group consisting of X, —CH$_2$CH (OH)CH$_2$—, and mixtures thereof; each v is from 0 to about 200; each w is from 0 to about 50, and v is equal or larger than w; each g and k is from 0 to about 10; j is g+k−1, providing that no O—O bonds are formed;
each R$^1$ group is selected from the same or different group and is selected from the group consisting of R, A, B, and D;
each a and b is an integer from 0 to 3;
m is from about 5 to about 1600;
n, a, and b, and the R$^1$ groups are selected such that the silicone polymer comprises at least one reactive Si functional group in the form of an Si—A group, selected from the group consisting of Si—H, Si—OH, Si—OR, Si—OCOR, and mixtures thereof; wherein a ratio of n to (m+n) is from 0 to about 1:2; and when p is not 0, a ratio of n to (m+n+p) is from 0 to about 1:2;
p, a, and b, and the R$^1$ groups are selected such that the silicone polymer optionally comprises at least one cationic group in the form of an Si—B group; wherein a ratio of p to (m+n+p) is from 0 to about 1:2;
q, a, and b, and the R$^1$ groups are selected such that the silicone polymer optionally comprises at least one poly(ethyleneoxy/propyleneoxy) Si—D group; wherein a ratio of q to (m+n+p+q) is from about 1:1000 to about 1:3; and
r is from 0 to about 100, with r being 0 when neither a polyalkyleneoxy group nor a cationic group is part of the polymer backbone; and when one or more polyalkyleneoxy groups and/or cationic groups are part of the polymer backbone, a ratio of r to (m+n+p) is from about 1:1000 to about 1:2;
wherein the different —O—SiR$_2$—, —O—SiRA—, —O—SiRB—, and —O—SiRD— groups can be distributed randomly in the silicone backbone and/or organized as block copolymers of different degrees.

2. The silicone polymer of claim 1, wherein R is selected from the group consisting of methyl, ethyl, propyl, butyl, phenyl, and mixtures thereof.

3. The silicone polymer of claim 2, wherein R is methyl.

4. The silicone polymer of claim 1, wherein said hydrocarbon or oxygenated hydrocarbon linking group X is selected from the group consisting of —CH$_2$CH$_2$CH$_2$—, —CH$_2$CH$_2$—, —CH$_2$CH(OH)CH$_2$OCH$_2$CH$_2$CH$_2$—, and —CH$_2$-phenylene-CH$_2$CH$_2$—, and mixtures thereof, and said cationic nitrogen functional group E is selected from the group consisting of amino group and quaternary ammonium derivatives thereof; cyclic amino group and quaternary ammonium derivatives thereof; imidazole group and imidazolium derivatives thereof; imidazoline group and imidazolinium derivatives thereof; polycationic group; and mixtures thereof.

5. The silicone polymer of claim 4, wherein said cationic nitrogen functional group E is selected from the group consisting of imidazole group, imidazolium group, imidazoline group, imidazolinium group, polycationic group, and mixtures thereof.

6. The silicone polymer of claim 1, wherein when Z is a hydrocarbon or oxygenated hydrocarbon linking group, Z is selected from the group consisting of —CH$_2$CH$_2$CH$_2$—, —CH$_2$CH$_2$—, —CH$_2$CH(OH)CH$_2$OCH$_2$CH$_2$CH$_2$—, -phenylene-CH$_2$CH$_2$— and —CH$_2$-phenylene-CH$_2$CH$_2$—, and mixtures thereof; when Z is an aminohydrocarbon linking group, Z is —CH$_2$CH$_2$CH$_2$—N— group; said c is at least about 2, said total c is from about 6 to about 1000; said c is larger than said d, total d is from 0 to about 300; and said e is from 1 to about 20.

7. The silicone polymer of claim 6, wherein said c is at least about 11, said total c is from about 11 to about 800 and said total d is from 0 to about 100.

8. The silicone polymer of claim 7, wherein said each c is at least about 21, total c is from about 21 to about 500.

9. The silicone polymer of claim 6, wherein said R$^3$ group is not hydrogen.

10. The silicone polymer of claim 6, wherein said R$^3$ group is selected from the group consisting of —R; —CH$_2$CH(R)OH; —CH$_2$C(R)$_2$OH; —CH$_2$CH(OH) CH$_2$OR; —CH$_2$CH(OH)CH$_2$(OCH$_2$CH$_2$)$_e$OR; —CH(R) OR, C(O)H, —C(O)R; tetrahydropyranyl group; amino group and quaternary ammonium derivatives thereof; cyclic amino group and quaternary ammonium derivatives thereof; imidazole group and imidazolium derivatives thereof; imidazoline group and imidazolinium derivatives thereof; and mixtures thereof; with R being selected from the group consisting of methyl, ethyl, propyl, butyl, phenyl, and mixtures thereof; and e is from 1 to about 20.

11. The silicone polymer of claim 10, wherein said $R^3$ group is selected from the group consisting of methyl group, ethyl group, and mixtures thereof.

12. The silicone polymer of claim 1, wherein said each $R^3$ group is a cationic nitrogen functional E group, and each c is at least about 11.

13. The silicone polymer of claim 12, wherein each c is at least about 15.

14. The silicone polymer of claim 13, wherein each c is at least about 30.

15. The silicone polymer of claim 12, wherein said each $R^3$ group is selected from the group consisting of amino group and quaternary ammonium derivatives thereof; cyclic amino group and quaternary ammonium derivatives thereof; imidazole group and imidazolium derivatives thereof; imidazoline group and imidazolinium derivatives thereof; tetrahydropyranyl group; and mixtures thereof.

16. The silicone polymer of claim 1, wherein said $R^3$ group is hydrogen, and each c is at least about 11.

17. The silicone polymer of claim 16, wherein each c is at least about 15.

18. The silicone polymer of claim 17, wherein each c is at least about 30.

19. The silicone polymer of claim 1, wherein said $R^3$ capping group is selected from the group consisting of hindered tertiary alcohol group, hindered secondary alcohol group, and mixtures thereof.

20. The silicone polymer of claim 1, wherein said linking group Z is an aminohydrocarbon linking group.

21. The silicone polymer of claim 20, wherein said aminohydrocarbon linking group Z is —CH$_2$CH$_2$CH$_2$—N— group; said total c is from about 6 to about 1000; and said total d is from 0 to about 300.

22. The silicone polymer of claim 1, wherein said A is selected from the group consisting of —CH$_2$CH$_2$Si(OR)$_3$, —CH$_2$CH$_2$Si(OR)$_2$R, —CH$_2$CH$_2$Si(OR)R$_2$, and mixtures thereof, and wherein each n, p, and q is at least 1.

23. The silicone polymer of claim 1, wherein m is from about 8 to about 400; the n to (m+n) ratio is from about 1:400 to about 1:4; the n to (m+n+p) ratio is from about 1:400 to about 1:4; the p to (m+n+p) ratio is from about 1:200 to about 1:3; and the q to (m+n+p) ratio is from about 1:200 to about 1:4.

24. The silicone polymer of claim 1, wherein each g and k is from about 1 to about 2.

25. The silicone polymer of claim 1, wherein each a and/or b is 1 or 2.

26. The silicone polymer of claim 1, wherein r is 0.

27. The silicone polymer of claim 1, wherein r is from 1 to about 10.

28. The silicone polymer of claim 27, wherein p is 0.

29. The silicone polymer of claim 27, wherein q is 0.

30. The silicone polymer of claim 1, wherein n is 0 and $R^1$ does not comprise A group.

31. The silicone polymer of claim 30, wherein said $R^3$ group is selected from the group consisting of —H; —R; —CH$_2$CH(R)OH; —CH$_2$C(R)$_2$OH; —CH$_2$CH(OH)CH$_2$OR; —CH$_2$CH(OH)CH$_2$(OCH$_2$CH$_2$)$_e$OR; —CH(R)OR, C(O)H, —C(O)R; tetrahydropyranyl group; amino group and quaternary ammonium derivatives thereof; cyclic amino group and quaternary ammonium derivatives thereof; imidazole group and imidazolium derivatives thereof; imidazoline group and imidazolinium derivatives thereof; and mixtures thereof; with R being selected from the group consisting of methyl, ethyl, propyl, butyl, phenyl, and mixtures thereof; and e is from 1 to about 20.

32. The silicone polymer of claim 30, wherein m is from about 8 to about 400; the p to (m+p) ratio is from about 1:200 to about 1:3; and the q to (m+p) ratio is from about 1:200 to about 1:4.

33. The silicone polymer of claim 1, wherein said polymer comprises at least two types of polyalkyleneoxy groups selected from the group consisting of terminal group, pendant group, internal polyalkyleneoxy group, and mixtures thereof.

34. The silicone polymer of claim 1, wherein said polymer comprises at least two types of cationic nitrogen groups, selected from the group consisting of pendant group, internal group, terminal group, terminal group on the end of a polyalkeneoxy terminal or pendant group, and mixtures thereof.

35. An anhydrous composition comprising the silicone polymer of claim 1.

36. The composition of claim 35, in the form of a gel, wax, powder, and/or liquid composition.

37. The composition of claim 36, in the form of a liquid further comprising a low molecular weight monohydric alcohol.

38. The composition of claim 37, in the form of a concentrated liquid composition to be diluted with water for use.

39. The composition of claim 35, additionally comprising other reactive silicones and/or silanes.

40. The composition of claim 39, wherein said other reactive silicones and/or silanes are selected from the group consisting of 3-aminopropyltrimethoxysilane, 3-aminopropylmethyldimethoxysilane, tetraethoxysilane, diacetoxymethyl terminated polydimethylsiloxanes, and mixtures thereof.

41. The composition of claim 35, to provide a benefit selected from the group consisting of fiber and fabric care, hair care, skin care, pet care, hard surface care, soft surface care, and car care.

42. An article of manufacture comprising the composition of claim 35, in a package, in association with instructions for use which direct the consumer to properly apply at least an effective amount of said silicone polymer to a surface to provide the desired benefits.

43. The article of claim 42, wherein said surface is fabric and said desired benefits include at least one of following long lasting fabric care benefits: wrinkle control, wrinkle resistance, fabric wear reduction, fabric wear resistance, fabric pilling reduction, fabric color maintenance, fabric color fading reduction, fabric color restoration, fabric softness, fabric soiling reduction, fabric soil release, fabric shape retention, ease of ironing, fabric comfort, fabric hydrophilicity, static control, and/or fabric shrinkage reduction.

44. A method for providing a fabric with a fabric care benefit selected from the group consisting of: wrinkle control, wrinkle resistance, fabric wear reduction, fabric wear resistance, fabric pilling reduction, fabric color maintenance, fabric color fading reduction, fabric color restoration, fabric softness, fabric soiling reduction, fabric soil release, fabric shape retention, ease of ironing, fabric comfort, fabric hydrophilicity, static control, and fabric shrinkage reduction, wherein said method comprises contacting said fabric with an effective amount silicone polymer of claim 1.

45. A method for providing a fabric with a fabric care benefit selected from the group consisting of: wrinkle control, wrinkle resistance, fabric wear reduction, fabric wear resistance, fabric pilling reduction, fabric color maintenance, fabric color fading reduction, fabric color restoration, fabric softness, fabric soiling reduction, fabric soil release, fabric shape retention, ease of ironing, fabric comfort, fabric hydrophilicity, static control, and fabric shrinkage reduction, wherein said method comprises contacting said fabric with an effective amount silicone polymer wherein said silicone polymer is provided by using the composition of claim 35.

* * * * *